US011440951B2

United States Patent
Thullier et al.

(10) Patent No.: US 11,440,951 B2
(45) Date of Patent: Sep. 13, 2022

(54) THERAPEUTIC ANTIBODIES TO MARBURG VIRUS

(71) Applicants: The Government of the United States, as Represented by the Secretary of the Army, Fort Detrick, MD (US); Philippe Thullier, Bernin (FR)

(72) Inventors: Philippe Thullier, Bernin (FR); Jeffrey Froude, II, Frederick, MD (US); John Dye, Jr., Frederick, MD (US)

(73) Assignee: THE GOVERNMENT OF THE UNITED STATES, AS REPRESENTED BY THE SECRETARY OF THE ARMY, Fort Detrick, MD (US)

( * ) Notice: Subject to any disclaimer, the term of this patent is extended or adjusted under 35 U.S.C. 154(b) by 235 days.

(21) Appl. No.: 16/491,672

(22) PCT Filed: Mar. 9, 2018

(86) PCT No.: PCT/US2018/021759
§ 371 (c)(1),
(2) Date: Sep. 6, 2019

(87) PCT Pub. No.: WO2018/169785
PCT Pub. Date: Sep. 20, 2018

(65) Prior Publication Data
US 2020/0407428 A1 Dec. 31, 2020

Related U.S. Application Data

(60) Provisional application No. 62/470,414, filed on Mar. 13, 2017.

(51) Int. Cl.
*C07K 16/10* (2006.01)
*A61P 31/14* (2006.01)
*A61K 39/42* (2006.01)
*A61K 39/00* (2006.01)

(52) U.S. Cl.
CPC .............. *C07K 16/10* (2013.01); *A61K 39/42* (2013.01); *A61P 31/14* (2018.01); *A61K 2039/507* (2013.01); *C07K 2317/24* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,800,815 A | 9/1998 | Chestnut et al. | |
| 7,563,443 B2 | 7/2009 | Grant et al. | |
| 7,740,850 B2 | 6/2010 | Zhu et al. | |
| 8,344,109 B2 | 1/2013 | Thullier et al. | |
| 8,535,668 B2 | 9/2013 | Thullier et al. | |
| 8,895,010 B2 | 11/2014 | Nadler et al. | |
| 9,017,668 B2 | 4/2015 | Kauvar et al. | |
| 9,169,318 B2 | 10/2015 | Horowitz et al. | |
| 2010/0221267 A1 | 9/2010 | Zhu et al. | |
| 2011/0300157 A1 | 12/2011 | Devy | |
| 2014/0302517 A1 | 10/2014 | Jung et al. | |
| 2014/0356354 A1 | 12/2014 | Lai et al. | |

FOREIGN PATENT DOCUMENTS

WO  WO-2015/127136 A2  8/2015

OTHER PUBLICATIONS

Bowers, E., et al., "Immunoglobulin G heavy chain variable region, partial [*Homo sapiens*]," GenBank: AEX28383.1, 2014.
Bowers, Elisabeth, et al., "Decreased Mutation Frequencies among Immunoglobulin G Variable Region Genes during Viremic HIV-1 Infection," PLoS ONE 9(1): e81913. doi:10.1371/journal.pone. 0081913, 2014, 13 pages.
Bradley, T., et al., "Immunoglobulin heavy chain variable region, partial [*Macaca mulatta*]," GenBank: ALW83517.1, 2016.
Bradley, Todd, et al., "Structural Constraints of Vaccine-Induced Tier-2 Autologous HIV Neutralizing Antibodies Targeting the Receptor Binding Site," *Cell Rep*. 14(1): 43-54, Jan. 5, 2016.
Corcoran, M.M., et al., "Immunoglobulin heavy chain variable region, partial [*Macaca mulatta*]," GenBank: ANZ54830.1, NCBI, 2016.
Kuwata, T., "Immunoglobulin kappa light chain, partial [*Macaca mulatta*], GenBank: AER46542.1," 2016.
Kuwata, T., "Immunoglobulin kappa light chain, partial [*Macaca mulatta*]," GenBank: AER46532.1, 2016.
Pelat, Thibaut, et al., "Isolation of a human-like antibody fragment (scFv) that neutralizes ricin biological activity," BMC Biotechnology 9:60, 2009.
Thullier, P., et al., "Anti-ricin immunoglobulin kappa light chain variable region, partial [*Macaca fascicularis*]," GenBank: ACI25428. 1, 2016.
Thullier, P., et al., "Anti-ricin immunoglobulin heavy chain variable region, partial [*Macaca fascicularis*]," GenBank: ACI25427.1, 2016.
Wang, Y., et al., "Immunoglobulin G light chain variable region, partial [*Macaca mulatta*]," GenBank: AMS25370.1, 2016.

(Continued)

*Primary Examiner* — Gary B Nickol
*Assistant Examiner* — Jegatheesan Seharaseyon
(74) *Attorney, Agent, or Firm* — Faegre Drinker Biddle & Reath LLP

(57) ABSTRACT

Provided here are immunoglobulins and compositions containing one or more of said immunoglobulins reactive to a strain of Marburg virus. The immunoglobulins and compositions comprising said immunoglobulins can be used prophylactically to prevent a Marburg virus infection or to treat a patient that has been exposed to a Marburg virus in order to reduce a symptom.

19 Claims, 16 Drawing Sheets
Specification includes a Sequence Listing.

(56) References Cited

OTHER PUBLICATIONS

Wang, Yimeng, et al., "High-Resolution Longitudinal Study of HIV-1 Env Vaccine-Elicited B Cell Responses to the Virus Primary Receptor Binding Site Reveals Affinity Maturation and Clonal Persistence," The Journal of Immunology; 196, pp. 3729-3743, 2016.

International Search Report / Written Opinion dated Aug. 29, 2018 for PCT/US2018/021759.

International Preliminary Report on Patentability for International Application No. PCT/US2018/021759 dated Sep. 26, 2019.

FIG. 1A

Heavy and Light Chain Antibody Sequences

R3F6 - Variable Heavy Sequence
QVQLLESGGDLVQPGESLRLSCVASGISFSNHGMTWVRQAPGKGLDWVSSIDSDGGGTFYADSVKGRFT
ISRDNSNNTVSLQMNSLRAEDTAVYFCAARHEYSDYYWGQGVLVTVSS (SEQ ID NO: 1)

R3F6 - Variable Light Sequence
EIELTQSPSTLSVSPGEKATLSCRASQSVGSRLAWYHQSPGQAPRLLIYGASSRPTGIPDRFSASGSGT
EFTLTISSLEPEDVGLYYCQQNSKWPLTFGGGTKVEIK(SEQ ID NO: 2)

R4G2 - Variable Heavy Sequence
EVQLMQSGRALVQPGESLRLSCVVSGLSFINHGVTQVRQAPGKMLDWVSSTDTAGGGPFCVDSVKDRFT
ISTDDSKNTVSLEINSMRVEDTAAYYCATRQEYSDYYWGRGVPVTVSS (SEQ ID NO: 3)

R4G2 - Variable Light Sequence
EIELTQSPSTLSASPGERVTLSCRASQSVGSRLAWYHQSPGQAPRLLIYGASSRPTGIPDRFSASGSGT
EFTLTISSLEPEDVGLYYCQQNYKWPLTFGGGTKVEIK (SEQ ID NO: 4)

R4A1 - Variable Heavy Sequence
QVQLVESGGGLVKPGGSLRLSCAASGFTFTDYYMDWIRQAPGKGLEWVSRISPGGDVTWYADSVKGRFT
ISRDNAQSLYLQMNSLRAEDTAVYFCARDDIVVSRIFDDWGQGTLVTVSS (SEQ ID NO: 5)

R4A1 - Variable Light Sequence
DIQMTQSPSSLSASVGDRVTITCRASQSIRSYLAWYQQKPGKAPKLLIYDAAHLESGVPSRFSGSGSGT
EFTLTISSLQPDDFATYYCQQRNSYPLTFGGGTKVEIK (SEQ ID NO: 6)

R4B11 - Variable Heavy Sequence
QVQLEQSGAEVREPGASVKVSCKASGLTSGSYAITWVRQAPGQGLEWMGVIIPLVGVTNYAEKFQGRVT
FTADTSTSTAYMELTSLRSDDTATYYCARDPFCSGNGCYGYYDVWGPGVKVTVSS(SEQ ID NO: 7)

R4B11 - Variable Light Sequence
DIELTQSPSSLSASVGDRVTITCRASQDISSWLAWYQQKPGKAPKLLISSASTLQSGVPSRFSGSGSGT
DFTLTINSLQSEDFATYYCQQYNSVPLTFGGGTKVEMK(SEQ ID NO: 8)

R4G7 - Variable Heavy Sequence
EVQLLESGGDLVQPGESLRLSCVVSGISFSNHGMTWVRQAPGKGLDWVSSIDSDGGGTFYADSVKGRFT
ISRDDSNNTVSLQMNSLRVEDTAVYYCAARHEYSDYYWGRGVPVTVSS (SEQ ID NO: 9)

R4G7 - Variable Light Sequence
DIELTQSPSILSVSPGERATLSCRASQSVGNRLAWYHQRPGQAPRLLIYGASSRPTGIPDRFSASGSGT
EFTLTISSLEPEDVGVYYCQQNSKWPLTFGGGTKVEIK (SEQ ID NO: 10)

R4G10 - Variable Heavy Sequence
EVQLVESGRACIQPGESLRLSCVIYGLSFSNHGVTQVRQATGKVLDWVCSTDTDGGGTCCVDSVKDRFT
ISRDDSKNTVSLEMNSMRVEDTAAYYCATRQEYSDYYWGRGVPVTVSS(SEQ ID NO: 11)

R4G10 - Variable Light Sequence
EIELTQSPSTLSASPGERVTLSCRASQSVGSRLAWYHQSPGQAPRLLIYGASSRPTGIPDRFSASGSGT
EFTLTISSLEPEDVGLYYCQQNYKWPLTFGGGTKVEIK (SEQ ID NO: 12)

R4G11 - Variable Heavy Sequence
EVQLVQSGGGLVQPGESLRLSCVVSGLSFSNHGVTWVRQAPGKGLDWVSSIDTDGGGTFYGDSVKGRFT
ISRDDSKN

FIG. 1B

TVSLEMNSLRVEDTAVYYCAARQEYSDYYWGRGVPVTVSS (SEQ ID NO: 13)

R4G11 - Variable Light Sequence
DIELTQSPSTLSVSPGERATLSCRASQSVGSRLAWYHQRPGQAPRLLIYGASSRPTGIPDRFSGSGSGT
EFTLTISSLEPEDVGLYYCQQNSKWPLTFGGGTKVEIK(SEQ ID NO: 14)

R3C4 - Variable Heavy Sequence
QVQLEQSGAEVKKPGASVKVSCKASGFTSGSYAISWVRQAPGQGLEWMGVIIPLVGVTNYAEKFQGRVT
FTADTSTSTAYMELSSLRSEDTATYFCARDPYCSGNGCYGWYDVWGPGVLVTVSS (SEQ ID NO: 15)

R3C4 - Variable Light Sequence
DIELTQSPSSLSASVGDKVTISCRASQYIKSWLAWYQQKPGKAPKLLIYKASSLQSGVPSRFSGSGSGT
DFTLTITNVQPEDFATYYCQQYDSAPFTFGPGTKLDIR(SEQ ID NO: 16)

R4G8 - Variable Heavy Sequence
EVQLVESGGGLVQPGESLRLSCVVSGLSFSNHGVTWVRQAPGKGLDWVSSIDTDGGGTFYGDSVKGRFT
ISRDNSKSTVSLEMNSLRVEDTAVYYCAARQEYSDYYWGRGVLVTVSS(SEQ ID NO: 17)

R4G8 - Variable Light Sequence
DIELTQSPAILSLSPGERATLLCRASQNVGNRLAWYHQRPGQAPRLLIYGASSRPTGIPDRFSGSGSGT
EFTLTISSLEPEDVGVYYCQQDSNWPLTFGGGTRVEIK (SEQ ID NO: 18)

R3D4 - Variable Heavy Sequence
QVQLVESGGGLVQPGESLRLSCVVSGLSFSNHGVTWVRQAPGKGLDWVSSIDTDGGGTFYGDSVKGRFT
ISRDNSKSTVSLEMNSLRVEDTAVYYCAARQEYSDYYWGRGVLVTVSS (SEQ ID NO: 19)

R3D4 - Variable Light Sequence
EIELTQSPSTLSVSPGERATLSCRASQSVGSRLAWYHQSPGQAPRLLIYGASSRPTGIPDRFSASGSGT
EFTLTISSLEPEDVGLYYCQQNSKWPLTFGGGTKVEIK(SEQ ID NO: 20)

R3G2 - Variable Heavy Sequence
EVQLVQSGGALVQPGESLRLSCVVSGLSFSNHGVTRVRQAPGKGLDWVSSTDTDGGGTFYGDSVKGRFT
ISRDDSKNTVSLEMNSLRVEDTAAYYCAARQEYSDYYWGRGVPVTVSS(SEQ ID NO: 21)

R3G2 - Variable Light Sequence
EIELTQSPSTLSVSPGERATLSCRASQSVGSRLAWYHQSPGQAPRLLIYGASSRPTGIPDRFSASGSGT
EFTLTISSLEPEDVGLYYCQQNYKWPLTFGGGTKVEIK(SEQ ID NO: 22)

R3G5 - Variable Heavy Sequence
QVQLLESGPGLVKPSETLSLNCTVTGDTLYGGFGWGWIRQPPGKGLEWIGNIYSHDGSTFYNPSLKGRV
SISTDTSKNQFSLRMDSVSAADAAVYFCVRSRSTHYYSGTYSHSFYYWGQGVLVSVSS(SEQ ID NO: 23)

R3G5 - Variable Light Sequence
EIELTQSPSPLSVSVGDKVTITCRASQDISSYLTWYQQKPGKACKLLISAASSLQSGVPSRFSGSGSGT
DFTLTIDSLQPEDFGTYYCQQYYSAPLFFGGGTKVEIK(SEQ ID NO: 24)

R4H12 - Variable Heavy Sequence
QVQLLESGGGLVQPGESLRLSCVVSGLSFSNHGVTWVRQAPGKGLDWVSSIDTDGGGTFYGDSVKGRFT
ISRDDSKNTVSLEMNSLRVEDTAVYYCAARQEYSDYYWGRGVPVTVSS(SEQ ID NO: 25)

R4H12 - Variable Light Sequence
EIELTQSPSTLSVSPGERATLSCRASQSVGSRLAWYHQSPGQAPRLLIYGASSRPTGIPDRFSASGSGT
EFTLTISSLEPEDVGLYYCQQNSKWPLTFGGGTKVEIK (SEQ ID NO: 26)

FIG. 1C

R3H2 - Variable Heavy Sequence
EVQLLESGGGLVQPGESLRLSCVVSGLSFSNHGVTWVRQAPGKGLDWVSSIDTDGGGTFYGDSVKGRFT
ISRDDSKNTVSLEMNSLRVEDTAVYYCAARQEYSDYYWGRGVPVTVSS(SEQ ID NO: 27)

R3H2 - Variable Light Sequence
DIELTQSPAILSLSPGERATLLCRASQNVGNRLAWYHQRPGQAPRLLIYGASSRPTGIPDRFSGSGSGT
EFTLTISSLEPEDVGVYYCQQDSNWPLTFGGGTRVEIK (SEQ ID NO: 28)

R4G9 - Variable Heavy Sequence
EVQLLESGGDLVQPGESLRLSCVASGISFSNHGMTWVRQAPGKGLDWVSSIDSDGGGTFYADSVKGRFT
ISRDNSNNTVSLQMNSLRAEDTAVYFCAARHEYSDYYWGQGVLVTVSS(SEQ ID NO: 29)

R4G9 - Variable Light Sequence
DIELTQSPAILSLSPGERATLLCRASQNVGNRLAWYHQRPGQAPRLLIYGASSRPTGIPDRFSGSGSGT
EFTLTISSLEPEDVGVYYCQQDSNWPLTFGGGTRVEIK (SEQ ID NO: 30)

R3H6 - Variable Heavy Sequence
EVQLLESGGGLVQPGESLRLSCVVSGLSFSNHGVTWVRQAPGKGLDWVSSIDTDGGGTFYGDSVKGRFT
ISRDDSKNTVSLEMNSLRVEDTAVYYCAARQEYSDYYWGRGVPVTVSS (SEQ ID NO: 31)

R3H6 - Variable Light Sequence
ELQMTQSPATLSLSPGERATLSCRASQSVGDRLAWYHQSPGQAPRLLIYGASNRPTGISDRFRGSGSGT
EFILTISSLEPEDVGVYYCQQDSSWPLTFGGGTKVEIK (SEQ ID NO: 32)

R3H10 - Variable Heavy Sequence
EVQLLESGGGLVQPGESLRLPCAASGFTFSGYGMSWVRQAPGKGLEWVSSIDSSGGETYYADSVKGRFT
ISRDNSKNMLYLQMNNLRAEDTAVYYCAARHEYSDYYWGQGVLVTVSS (SEQ ID NO: 33)

R3H10 - Variable Light Sequence
DIELTQSPSTLSVSPGERATLSCRASQSVGSRLAWYHQSPGQAPRLLIYGASSRPTGIPDRFSASGSGT
EFTLTISSLEPEDVGLYYCQQNSKWPLTFGGGTKVEIK (SEQ ID NO: 34)

R4H11 - Variable Heavy Sequence
EVQLVQSGGGLVQPGESLRLSCVVSGLSFSNHGVTWVRQAPGKGLDWVSSIDTDGGGTFYGDSVKGRFT
ISRDDSKNTVSLEMNSLRVEDTAVYYCAARQEYSDYYWGRGVPVTVSS (SEQ ID NO: 35)

R4H11 - Variable Light Sequence
EIELTQSPSTLSVSPGERATLSCRASQSVGSRLAWYHQSPGQAPRLLIYGASSRPTGIPDRFSASGSGT
EFTLTISSLEPEDVGLYYCQQNSKWPLTFGGGTKVEIK (SEQ ID NO: 36)

MARV Sequences for Patent with CDRs identified for VH/VL in BOLD

```
>R4A1 VH
QVQLVESGGGLVKPGGSLRLSCAASGFTFTDYYMDWIRQAPGKGLEWVSRISPGGDVTWYADSVKGRFTI
SRDNAQSLYLQMNSLRAEDTAVYFCARDDIVVSRIFDDWGQGTLVTVSS
>R4A1 VL
DIQMTQSPSSLSASVGDRVTITCRASQSIRSYLAWYQQKPGKAPKLLIYDAAHLESGVPSRFSGSGSGTE
FTLTISSLQPDDFATYYCQQRNSYPLTFGGGTKVEIK

>R4G2 VH
EVQLMQSGRALVQPGESLRLSCVVSGLSFINHGVTQVRQAPGKMLDWVSSTDTAGGGPFCVDSVKDRFTI
STDDSKNTVSLEINSMRVEDTAAYYCATRQEYSDYYWGRGVPVTVSS
>R4G2 VL
EIELTQSPSTLSASPGERVTLSCRASQSVGSRLAWYHQSPGQAPRLLIYGASSRPTGIPDRFSASGSGTE
FTLTISSLEPEDVGLYYCQQNYKWPLTFGGGTKVEIK

>R3F6 VH
QVQLLESGGDLVQPGESLRLSCVASGISFSNHGMTWVRQAPGKGLDWVSSIDSDGGGTFYADSVKGRFTI
SRDNSNNTVSLQMNSLRAEDTAVYFCAARHEYSDYYWGQGVLVTVSS
>R3F6 VL
EIELTQSPSTLSVSPGEKATLSCRASQSVGSRLAWYHQSPGQAPRLLIYGASSRPTGIPDRFSASGSGTE
FTLTISSLEPEDVGLYYCQQNSKWPLTFGGGTKVEIK

>R4B11 VH
QVQLEQSGAEVREPGASVKVSCKASGLTSGSYAITWVRQAPGQGLEWMGVIIPLVGVTNYAEKFQGRVTF
TADTSTSTAYMELTSLRSDDTATYYCARDPFCSGNGCYGYYDVWGPGVKVTVSS
>R4B11 VL
DIELTQSPSSLSASVGDRVTITCRASQDISSWLAWYQQKPGKAPKLLISSASTLQSGVPSRFSGSGSGTD
FTLTINSLQSEDFATYYCQQYNSVPLTFGGGTKVEMK

>R4G7 VH
EVQLLESGGDLVQPGESLRLSCVVSGISFSNHGMTWVRQAPGKGLDWVSSIDSDGGGTFYADSVKGRFTI
SRDDSNNTVSLQMNSLRVEDTAVYYCAARHEYSDYYWGRGVPVTVSS
>R4G7 VL
DIELTQSPSILSVSPGERATLSCRASQSVGNRLAWYHQRPGQAPRLLIYGASSRPTGIPDRFSASGSGTE
FTLTISSLEPEDVGVYYCQQNSKWPLTFGGGTKVEIK

>R4G10 VH
EVQLVESGRACIQPGESLRLSCVIYGLSFSNHGVTQVRQATGKVLDWVCSTDTDGGGTCCVDSVKDRFTI
SRDDSKNTVSLEMNSMRVEDTAAYYCATRQEYSDYYWGRGVPVTVSS
>R4G10 VL
EIELTQSPSTLSASPGERVTLSCRASQSVGSRLAWYHQSPGQAPRLLIYGASSRPTGIPDRFSASGSGTE
FTLTISSLEPEDVGLYYCQQNYKWPLTFGGGTKVEIK

>R4G11 VH
EVQLVQSGGGLVQPGESLRLSCVVSGLSFSNHGVTWVRQAPGKGLDWVSSIDTDGGGTFYGDSVKGRFTI
SRDDSKNTVSLEMNSLRVEDTAVYYCAARQEYSDYYWGRGVPVTVSS
>R4G11 VL
DIELTQSPSTLSVSPGERATLSCRASQSVGSRLAWYHQRPGQAPRLLIYGASSRPTGIPDRFSGSGSGTE
FTLTISSLEPEDVGLYYCQQNSKWPLTFGGGTKVEIK

QVQLEQSGAEVKKPGASVKVSCKASGFTSGSYAISWVRQAPGQGLEWMGVIIPLVGVTNYAEKFQGRVTF
TADTSTSTAYMELSSLRSEDTATYFCARDPYCSGNGCYGWYDVWGPGVLVTVSS
>R3C4 VL
DIELTQSPSSLSASVGDKVTISCRASQYIKSWLAWYQQKPGKAPKLLIYKASSLQSGVPSRFSGSGSGTD
FTLTITNVQPEDFATYYCQQYDSAPFTFGPGTKLDIR

>R4G8 VH
EVQLVESGGGLVQPGESLRLSCVVSGLSFSNHGVTWVRQAPGKGLDWVSSIDTDGGGTFYGDSVKGRFTI
SRDNSKSTVSLEMNSLRVEDTAVYYCAARQEYSDYYWGRGVLVTVSSASTKGPKLEEGEF
>R4G8 VL
DIELTQSPAILSLSPGERATLLCRASQNVGNRLAWYHQRPGQAPRLLIYGASSRPTGIPDRFSGSGSGTE
FTLTISSLEPEDVGVYYCQQDSNWPLTFGGGTRVEIK

>R3D4 VH
QVQLVESGGGLVQPGESLRLSCVVSGLSFSNHGVTWVRQAPGKGLDWVSSIDTDGGGTFYGDSVKGRFTI
SRDNSKSTVSLEMNSLRVEDTAVYYCAARQEYSDYYWGRGVLVTVSS
>R3D4 VL
EIELTQSPSTLSVSPGERATLSCRASQSVGSRLAWYHQSPGQAPRLLIYGASSRPTGIPDRFSASGSGTE
FTLTISSLEPEDVGLYYCQQNSKWPLTFGGGTKVEIK

>R3G2 VH
EVQLVQSGGALVQPGESLRLSCVVSGLSFSNHGVTRVRQAPGKGLDWVSSTDTDGGGTFYGDSVKGRFTI
SRDDSKNTVSLEMNSLRVEDTAAYYCAARQEYSDYYWGRGVPVTVSS
>R3G2 VL
EIELTQSPSTLSVSPGERATLSCRASQSVGSRLAWYHQSPGQAPRLLIYGASSRPTGIPDRFSASGSGTE
FTLTISSLEPEDVGLYYCQQNYKWPLTFGGGTKVEIK

>R3G5 VH
QVQLLESGPGLVKPSETLSLNCTVTGDTLYGGFGWGWIRQPPGKGLEWIGNIYSHDGSTFYNPSLKGRVS
ISTDTSKNQFSLRMDSVSAADAAVYFCVRSRSTHYYSGTYSHSFYYWGQGVLVSVSS
>R3G5 VL
EIELTQSPSPLSVSVGDKVTITCRASQDISSYLTWYQQKPGKACKLLISAASSLQSGVPSRFSGSGSGTD
FTLTIDSLQPEDFGTYYCQQYYSAPLFFGGGTKVEIK

>R4H12 VH
QVQLLESGGGLVQPGESLRLSCVVSGLSFSNHGVTWVRQAPGKGLDWVSSIDTDGGGTFYGDSVKGRFTI
SRDDSKNTVSLEMNSLRVEDTAVYYCAARQEYSDYYWGRGVPVTVSS
>R4H12 VL
EIELTQSPSTLSVSPGERATLSCRASQSVGSRLAWYHQSPGQAPRLLIYGASSRPTGIPDRFSASGSGTE
FTLTISSLEPEDVGLYYCQQNSKWPLTFGGGTKVEIK

>R3H2 VH
EVQLLESGGGLVQPGESLRLSCVVSGLSFSNHGVTWVRQAPGKGLDWVSSIDTDGGGTFYGDSVKGRFTI
SRDDSKNTVSLEMNSLRVEDTAVYYCAARQEYSDYYWGRGVPVTVSS
>R3H2 VL
DIELTQSPAILSLSPGERATLLCRASQNVGNRLAWYHQRPGQAPRLLIYGASSRPTGIPDRFSGSGSGTE
FTLTISSLEPEDVGVYYCQQDSNWPLTFGGGTRVEIK

>R4G9 VH
EVQLLESGGDLVQPGESLRLSCVASGISFSNHGMTWVRQAPGKGLDWVSSIDSDGGGTFYADSVKGRFTI
SRDNSNNTVSLQMNSLRAEDTAVYFCAARHEYSDYYWGQGVLVTVSS
>R4G9 VL
DIELTQSPAILSLSPGERATLLCRASQNVGNRLAWYHQRPGQAPRLLIYGASSRPTGIPDRFSGSGSGTE
FTLTISSLEPEDVGVYYCQQDSNWPLTFGGGTRVEIK

FIG. 12C

>R3H6 VH
EVQLLESGGGLVQPGESLRLSCVVS GLSFSNHG VTWVRQAPGKGLDWVSS IDTDGGGT FYGDSVKGRFTI
SRDDSKNTVSLEMNSLRVEDTAVYYC AARQEYSDYY WGRGVPVTVSS
>R3H6 VL
ELQMTQSPATLSLSPGERATLSCRAS QSVGDR LAWYHQSPGQAPRLLIY GAS NRPTGISDRFRGSGSGTE
FILTISSLEPEDVGVYYC QQDSSWPLT FGGGTKVEIK

>R3H10 VH
EVQLLESGGGLVQPGESLRLPCAAS GFTFSGYG MSWVRQAPGKGLEWVSS IDSSGGET YYADSVKGRFTI
SRDNSKNMLYLQMNNLRAEDTAVYYC AARHEYSDYY WGQGVLVTVSS
>R3H10 VL
DIELTQSPSTLSVSPGERATLSCRAS QSVGSR LAWYHQSPGQAPRLLIY GAS SRPTGIPDRFSASGSGTE
FTLTISSLEPEDVGLYYC QQNSKWPLT FGGGTKVEIK

>R4H11 VH
EVQLVQSGGGLVQPGESLRLSCVVS GLSFSNHG VTWVRQAPGKGLDWVSS IDTDGGGT FYGDSVKGRFTI
SRDDSKNTVSLEMNSLRVEDTAVYYC AARQEYSDYY WGRGVPVTVSS
>R4H11 VL
EIELTQSPSTLSVSPGERATLSCRAS QSVGSR LAWYHQSPGQAPRLLIY GAS SRPTGIPDRFSASGSGTE
FTLTISSLEPEDVGLYYC QQNSKWPLT FGGGTKVEIK

THERAPEUTIC ANTIBODIES TO MARBURG VIRUS

REFERENCE TO RELATED APPLICATIONS

This application is the National Stage of International Application No. PCT/US2018/021759, filed Mar. 9, 2018, and claims benefit to U.S. Provisional Application No. 62/470,414 filed Mar. 22, 2017, both of which are incorporated by reference in their entirety.

STATEMENT REGARDING FEDERALLY SPONSORED RESEARCH OR DEVELOPMENT

The materials and methods described herein were made using U.S. Army Medical Research & Material Command funding. The Government has certain rights in the invention.

REFERENCE TO A SEQUENCE LISTING

The instant application contains a Sequence Listing which has been submitted electronically in ASCII format and is hereby incorporated by reference in its entirety. Said ASCII copy, created on Mar. 13, 2020, is named 200563_0024_00_US_587739_ST25.txt and is 40,615 bytes in size.

BACKGROUND

Marburg virus (MARV), together with the five members of the *Ebolavirus* genus, constitutes the family Filoviridae of the order Mononegravirales. MARV causes severe and highly lethal viral hemorrhagic fevers (VHF) in both non-human primates (NHP) and humans (Kuhn R. J., "*Togaviridae: The Viruses and Their Replication*," IN KNIPE D M, HOWLEY P M, EDS. FIELDS VIROLOGY 1001-22 (5 ed. Philadelphia: Lippincott Williams & Wilkins 2007). The primary transmission of MARV is through contact with infected bodily fluids from infected humans or animals (MacNeil A. et al., "Ebola and Marburg hemorrhagic fevers: neglected tropical diseases?," *PLoS Neglected Tropical Diseases* 2012 6(6): e1546). MARV was first identified in 1967 in Germany and Yugoslavia, and continues to cause sporadic outbreaks throughout equatorial Africa (Martini G. et al., editors. MARBURG VIRUS DISEASE—Congresses Springer-Verlag; 1971. p. 250). In the absence of a licensed vaccine or therapeutic, there are limited options beyond supportive care (Edwards T., et al., "Design and analysis considerations in the Ebola_Tx trial evaluating convalescent plasma in the treatment of Ebola virus disease in Guinea during the 2014-2015 outbreak," *Clinical Trials* 2016; 13(1): 13-21). Although several vaccine and a few therapeutic options are currently in clinical trials for non-Marburg filoviruses, these are specific only to EBOV. Additionally, issues with the logistics of a complete vaccination program present a strategic gap for this global threat and do not eliminate the need for a post-exposure therapeutic program (Froude J. W. et al., "Antibodies for biodefense," *mAbs* 2011; 3(6): 517-27).

Filoviruses are non-segmented, single-stranded, and their okay for this individual is my form generally is and will know negative sense RNA viruses that contain seven or more structural proteins (Bradfute, S. B., et al., "Filovirus vaccines," *Human Vaccines* 2011; 7(6): 701-11). The transmembrane glycoprotein (GP) is expressed on the viral surface and is the primary facilitating protein of entry into the host cells. The location and abundance of this protein on the virion surface makes it a candidate for the development of protective antibodies. However, vaccine candidates have shown varying degrees of success in animal models and in clinical trials (For reviews, see references 7-9). Initial attempts focused on the use of inactivated whole virus with mixed success in NHP models while later attempts utilized virus-like replicon particles (VRP), virus-like particles (VLP), viral vectors or plasmid DNA with greater levels of protection offered. See H. W. Lupton et al., "Inactivated vaccine for Ebola virus efficacious in guinea pig model," *Lancet* 1980; 2(8207): 1294-5; Sullivan, N. J., et al., "Development of a preventive vaccine for Ebola virus infection in primates," *Nature* 2000 408(6812): 605-9; Swenson, D. L., et al., "Virus like particles exhibit potential as a pan-filovirus vaccine for both Ebola and Marburg viral infections," *Vaccine* 2005; 23(23): 3033-42. The shared component of all these vaccine candidates was the concept of developing an immune response against GP, which would hopefully lead to the generation of protective antibodies and cellular responses.

Convalescent serum was used during the 1995 Kikwit Ebola outbreak, providing the first suggestion that an immunotherapeutic could be effective for the treatment of filovirus-infected individuals. In this small study (n=8), with no control group, convalescent serum treatment reduced mortality from 80% seen in the broader outbreak to 12.5%, although the authors acknowledge the possibility of a standard of care effect (Mupapa, K., et al., "Treatment of Ebola hemorrhagic fever with blood transfusions from convalescent patients," International Scientific and Technical Committee. *The Journal of infectious diseases* 1999; 179 Suppl 1: S18-23). Since that time, there has been expanding, yet limited, success in developing protective antibody-based therapeutics against filoviruses. The recombinant anti-EBOV antibody KZ52, isolated from a human survivor, was shown to be protective in guinea pig models; however, it failed to protect in the NHP model (Oswald, W. B., et al., "Neutralizing antibody fails to impact the course of Ebola virus infection in monkeys," *PLoS pathogens* 2007; 3(1): e9; Parren, P. W., et al., "Pre- and postexposure prophylaxis of Ebola virus infection in an animal model by passive transfer of a neutralizing human antibody. *J. Virology* 2002 76(12): 6408-12.). Dye et al. were the first to demonstrate the utility of antibody passive transfer therapies in NHP models of filovirus infections (Dye, J. M. et al., "Postexposure antibody prophylaxis protects nonhuman primates from filovirus disease," *Proc. Nat'l Acad. Sci. USA* 2012 109(13): 5034-9). EBOV- or MARV-infected NHPs were fully protected when treated with immunoglobulin G (IgG) purified from species-matched convalescent serum, even when treatment was delayed 48 hours post-infection. The first utilization of a monoclonal therapy for MARV has been recently reported by Fusco et al. where they found two mAbs which bind to GP, which were able to provide protection, but to a mouse-adapted Ravn strain of Marburg virus (RAVV) (Fusco, M. L. et al., "Protective mAbs and Cross-Reactive mAbs Raised by Immunization with Engineered Marburg Virus GPs," *PLoS pathogens* 2015; 11(6): e1005016)

SUMMARY

Therefore, there remains a need to identify high affinity antibodies or antibody fragments that target MARV GP. Such antibodies can also protect animal models from infection.

Provided herein is a composition comprising at least one reactive anti-Marburg immunoglobulin selected from the group consisting of:

a) an immunoglobulin comprising VH complementarity determining regions (CDRs) present in SEQ ID NO: 1 and VL CDRs present in SEQ ID NO: 2, wherein VH CDR1, CDR2 and CDR3 have at most a 2 amino acid substitution, deletion or addition, and wherein VL CDR1, CDR2 and CDR3 have at most a 2 amino acid substitution, deletion or addition;

b) an immunoglobulin comprising VH complementarity determining regions (CDRs) present in SEQ ID NO: 3 and VL CDRs present in SEQ ID NO: 4, wherein VH CDR1, CDR2 and CDR3 have at most a 2 amino acid substitution, deletion or addition, and wherein VL CDR1, CDR2 and CDR3 have at most a 2 amino acid substitution, deletion or addition;

c) an immunoglobulin comprising a VH as presented in SEQ ID NO: 5 and a VL as presented in SEQ ID NO: 6; and d) an immunoglobulin comprising VH complementarity determining regions (CDRs) present in SEQ ID NO: 7 and VL CDRs present in SEQ ID NO: 8, wherein VH CDR1, CDR2 and CDR3 have at most a 2 amino acid substitution, deletion or addition, and wherein VL CDR1, CDR2 and CDR3 have at most a 2 amino acid substitution, deletion or addition;

and a pharmaceutically acceptable carrier.

The provided an immunoglobulin of the composition is reactive with a strain of Marburg virus, for example with one or of Ci67, Ravn, Musoke, or Angola.

The composition can comprise the immunoglobulin comprising CDRs in SEQ ID NO: 1 and SEQ ID NO: 2 and at least one other immunoglobulin selected from the group consisting of:

(a) immunoglobulin R4G7 consisting of VH complementarity determining regions (CDRs) present in SEQ ID NO: 9 and VL CDRs present in SEQ ID NO: 10, wherein VH CDR1, CDR2 and CDR3 have at most a 2 amino acid substitution, deletion or addition, and wherein VL CDR1, CDR2 and CDR3 have at most a 2 amino acid substitution, deletion or addition;

(b) immunoglobulin R4G10 consisting of VH complementarity determining regions (CDRs) present in SEQ ID NO: 11 and VL CDRs present in SEQ ID NO: 12, wherein VH CDR1, CDR2 and CDR3 have at most a 2 amino acid substitution, deletion or addition, and wherein VL CDR1, CDR2 and CDR3 have at most a 2 amino acid substitution, deletion or addition;

(c) immunoglobulin R4G11 consisting of VH complementarity determining regions (CDRs) present in SEQ ID NO: 13 and VL CDRs present in SEQ ID NO: 14, wherein VH CDR1, CDR2 and CDR3 have at most a 2 amino acid substitution, deletion or addition, and wherein VL CDR1, CDR2 and CDR3 have at most a 2 amino acid substitution, deletion or addition;

(d) immunoglobulin R3C4 consisting of VH complementarity determining regions (CDRs) present in SEQ ID NO: 15 and VL CDRs present in SEQ ID NO: 16, wherein VH CDR1, CDR2 and CDR3 have at most a 2 amino acid substitution, deletion or addition, and wherein VL CDR1, CDR2 and CDR3 have at most a 2 amino acid substitution, deletion or addition;

(e) immunoglobulin R4G8 consisting of VH complementarity determining regions (CDRs) present in SEQ ID NO: 17 and VL CDRs present in SEQ ID NO: 18, wherein VH CDR1, CDR2 and CDR3 have at most a 2 amino acid substitution, deletion or addition, and wherein VL CDR1, CDR2 and CDR3 have at most a 2 amino acid substitution, deletion or addition;

(f) immunoglobulin R3D4 consisting of VH complementarity determining regions (CDRs) present in SEQ ID NO: 19 and VL CDRs present in SEQ ID NO: 20, wherein VH CDR1, CDR2 and CDR3 have at most a 2 amino acid substitution, deletion or addition, and wherein VL CDR1, CDR2 and CDR3 have at most a 2 amino acid substitution, deletion or addition;

(g) immunoglobulin R3G2 consisting of VH complementarity determining regions (CDRs) present in SEQ ID NO: 21 and VL CDRs present in SEQ ID NO: 22, wherein VH CDR1, CDR2 and CDR3 have at most a 2 amino acid substitution, deletion or addition, and wherein VL CDR1, CDR2 and CDR3 have at most a 2 amino acid substitution, deletion or addition;

(h) immunoglobulin R3G5 consisting of VH complementarity determining regions (CDRs) present in SEQ ID NO: 23 and VL CDRs present in SEQ ID NO: 24, wherein VH CDR1, CDR2 and CDR3 have at most a 2 amino acid substitution, deletion or addition, and wherein VL CDR1, CDR2 and CDR3 have at most a 2 amino acid substitution, deletion or addition;

(i) immunoglobulin R4H12 consisting of VH complementarity determining regions (CDRs) present in SEQ ID NO: 25 and VL CDRs present in SEQ ID NO: 26, wherein VH CDR1, CDR2 and CDR3 have at most a 2 amino acid substitution, deletion or addition, and wherein VL CDR1, CDR2 and CDR3 have at most a 2 amino acid substitution, deletion or addition; and (j) immunoglobulin R3H2 consisting of VH complementarity determining regions (CDRs) present in SEQ ID NO: 27 and VL CDRs present in SEQ ID NO: 28, wherein VH CDR1, CDR2 and CDR3 have at most a 2 amino acid substitution, deletion or addition, and wherein VL CDR1, CDR2 and CDR3 have at most a 2 amino acid substitution, deletion or addition.

Alternatively, the composition can comprise an immunoglobulin having the heavy and light chain sequence of R4G2.

The immunoglobulins of the compositions described herein can have at least 90%, at least 95%, at least 96%, at least 97%, at least 98%, at least 99% sequence, or 100% sequence identity respectively to VH and VL sequences of: (a) SEQ ID NO: 1 and 2, (b) SEQ ID NO: 3 and 4, (c) SEQ ID NO: 5 and 6, or (d) SEQ ID NO: 7 and 8. The composition can comprise an immunoglobulin, wherein the immunoglobulin is (i) R3F6 having a variable heavy chain of SEQ ID NO: 1 and a variable light chain of SEQ ID NO: 2; (ii) R4G2 having a variable heavy chain of SEQ ID NO: 3 and having a variable light chain of SEQ ID NO: 4; (iii) R4A1 having a variable heavy chain of SEQ ID NO: 5 and having a variable light chain of SEQ ID NO: 6, or (iv) R4B11 is having a variable heavy chain of SEQ ID NO: 7 and having a variable light chain of SEQ ID NO: 8.

The composition can comprise the immunoglobulins described herein wherein the immunoglobulin is in the form of a bispecific antibody, a scFv, a Fab, or a diabody. The immunoglobulin of the composition can be humanized. The immunoglobulin can be an IgG.

A method of protecting a subject from exposure to a Marburg virus strain is provided comprising administering to said subject an effective amount of a composition described herein prior to exposure to said Marburg virus. The subject can be a human. The method can further use a composition that comprises an immunoglobulin that is engineered for extended release, and wherein said the effective amount is an amount of about 5 to about 50 mg/kg of subject weight.

A method of inhibiting progression of a Marburg virus infection in a subject after the subject is exposed to the Marburg virus is also provided which comprises administering at least one effective amount of a composition described herein. The method of inhibiting progression of a Marburg virus infection can administer a composition as described herein wherein the effective amount of the composition is administered within one week after exposure to a Marburg virus, wherein the composition is administered intravenously (i.v.) or subcutaneously (s.c.) at a dosage of about 25 to about 150 mg/kg of subject weight.

For the described methods, the composition described herein can be administered once or more. For example, the composition can be administered two times.

Also disclosed is a use of a composition for treating or preventing a Marburg virus infection in a subject exposed to a Marburg virus strain.

An immunoglobulin is provided that is reactive to a strain of Marburg virus wherein the immunoglobulin is selected from the group consisting of:
a) an immunoglobulin comprising VH complementarity determining regions (CDRs) present in SEQ ID NO: 1 and VL CDRs present in SEQ ID NO: 2, wherein VH CDR1, CDR2 and CDR3 have at most a 2 amino acid substitution, deletion or addition, and wherein VL CDR1, CDR2 and CDR3 have at most a 2 amino acid substitution, deletion or addition;
b) an immunoglobulin comprising VH complementarity determining regions (CDRs) present in SEQ ID NO: 3 and VL CDRs present in SEQ ID NO: 4, wherein VH CDR1, CDR2 and CDR3 have at most a 2 amino acid substitution, deletion or addition, and wherein VL CDR, CDR2 and CDR3 have at most a 2 amino acid substitution, deletion or addition;
c) an immunoglobulin comprising a VH as presented in SEQ ID NO: 5 and a VL as presented in SEQ ID NO: 6; and
d) an immunoglobulin comprising VH complementarity determining regions (CDRs) present in SEQ ID NO: 7 and VL CDRs present in SEQ ID NO: 8, wherein VH CDR1, CDR2 and CDR3 have at most a 2 amino acid substitution, deletion or addition, and wherein VL CDR1, CDR2 and CDR3 have at most a 2 amino acid substitution, deletion or addition;
(e) immunoglobulin R4G7 consisting of VH complementarity determining regions (CDRs) present in SEQ ID NO: 9 and VL CDRs present in SEQ ID NO: 10, wherein VH CDR1, CDR2 and CDR3 have at most a 2 amino acid substitution, deletion or addition, and wherein VL CDR1, CDR2 and CDR3 have at most a 2 amino acid substitution, deletion or addition;
(f) immunoglobulin R4G10 consisting of VH complementarity determining regions (CDRs) present in SEQ ID NO: 11 and VL CDRs present in SEQ ID NO: 12, wherein VH CDR1, CDR2 and CDR3 have at most a 2 amino acid substitution, deletion or addition, and wherein VL CDR1, CDR2 and CDR3 have at most a 2 amino acid substitution, deletion or addition;
(g) immunoglobulin R4G11 consisting of VH complementarity determining regions (CDRs) present in SEQ ID NO: 13 and VL CDRs present in SEQ ID NO: 14, wherein VH CDR1, CDR2 and CDR3 have at most a 2 amino acid substitution, deletion or addition, and wherein VL CDR1, CDR2 and CDR3 have at most a 2 amino acid substitution, deletion or addition;
(h) immunoglobulin R3C4 consisting of VH complementarity determining regions (CDRs) present in SEQ ID NO: 15 and VL CDRs present in SEQ ID NO: 16, wherein VH CDR1, CDR2 and CDR3 have at most a 2 amino acid substitution, deletion or addition, and wherein VL CDR1, CDR2 and CDR3 have at most a 2 amino acid substitution, deletion or addition;
(i) immunoglobulin R4G8 consisting of VH complementarity determining regions (CDRs) present in SEQ ID NO: 17 and VL CDRs present in SEQ ID NO: 18, wherein VH CDR1, CDR2 and CDR3 have at most a 2 amino acid substitution, deletion or addition, and wherein VL CDR1, CDR2 and CDR3 have at most a 2 amino acid substitution, deletion or addition;
(j) immunoglobulin R3D4 consisting of VH complementarity determining regions (CDRs) present in SEQ ID NO: 19 and VL CDRs present in SEQ ID NO: 20, wherein VH CDR1, CDR2 and CDR3 have at most a 2 amino acid substitution, deletion or addition, and wherein VL CDR1, CDR2 and CDR3 have at most a 2 amino acid substitution, deletion or addition;
(k) immunoglobulin R3G2 consisting of VH complementarity determining regions (CDRs) present in SEQ ID NO: 21 and VL CDRs present in SEQ ID NO: 22, wherein VH CDR1, CDR2 and CDR3 have at most a 2 amino acid substitution, deletion or addition, and wherein VL CDR1, CDR2 and CDR3 have at most a 2 amino acid substitution, deletion or addition;
(l) immunoglobulin R3G5 consisting of VH complementarity determining regions (CDRs) present in SEQ ID NO: 23 and VL CDRs present in SEQ ID NO: 24, wherein VH CDR1, CDR2 and CDR3 have at most a 2 amino acid substitution, deletion or addition, and wherein VL CDR1, CDR2 and CDR3 have at most a 2 amino acid substitution, deletion or addition;
(m) immunoglobulin R4H12 consisting of VH complementarity determining regions (CDRs) present in SEQ ID NO: 25 and VL CDRs present in SEQ ID NO: 26, wherein VH CDR1, CDR2 and CDR3 have at most a 2 amino acid substitution, deletion or addition, and wherein VL CDR1, CDR2 and CDR3 have at most a 2 amino acid substitution, deletion or addition; and
(n) immunoglobulin R3H2 consisting of VH complementarity determining regions (CDRs) present in SEQ ID NO: 27 and VL CDRs present in SEQ ID NO: 28, wherein VH CDR1, CDR2 and CDR3 have at most a 2 amino acid substitution, deletion or addition, and wherein VL CDR1, CDR2 and CDR3 have at most a 2 amino acid substitution, deletion or addition.

BRIEF DESCRIPTION OF THE DRAWINGS

FIG. 1 provides the heavy and light chain sequences of the antibodies discussed.

FIG. 4 Western blots analysis of the reactivity of the scFv-Fc antibodies to whole irradiated virus. In the 4-12% gradient gel, each lane was loaded with 3 μL of a 1:500 dilution of sucrose purified Marburg virus isolates corresponding to the labeled well.

FIG. 5A depicts photographic representation of viral plaques and FIG. 5B depicts corresponding plaque sizes in Vero E6 cells. All plaque sizes were highly significant to a p-value<0.0001 by utilizing a two-tailed t-test for the four antibody fragments tested against control virus.

FIG. 12 depicts two antibodies by their heavy and light chains along with an indication in bold and in a box as to each CDR.

DESCRIPTION

Figure 2:
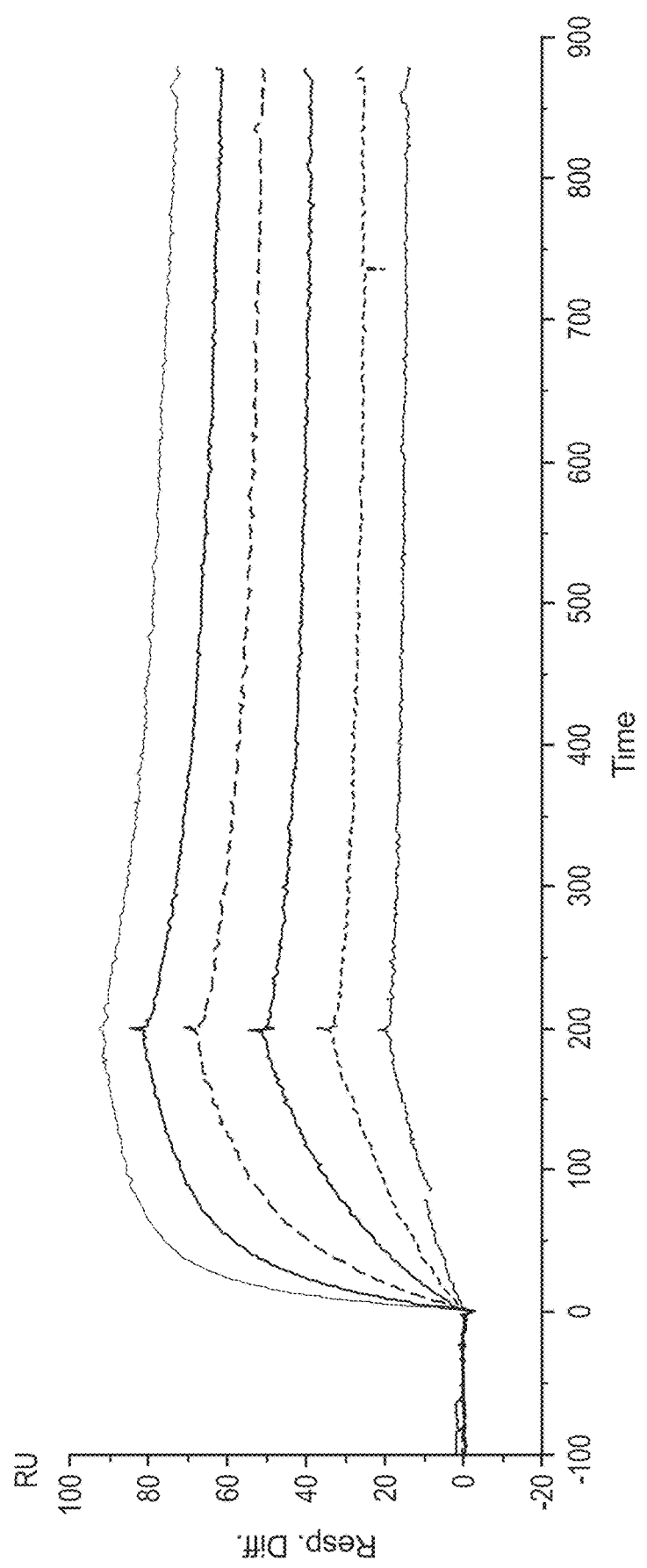
FIG. 2 is a representative BiaCore sensorgram of anti-MARV antibody scFv-R4A1. R4A1 affinity was measured at 4.4 nM against MARV GP, utilizing an 800 second elution.

Described herein is the isolation and characterization of the protective antibodies to wild-type MARV. Non-human primates (NHP), cynomolgus macaques, were immunized with viral-like particles expressing the glycoproteins (GP) of MARV (Ci67 isolate) at their surface. An antibody fragment (single chain variable fragment, scFv) phage display library was built after four immunogen injections, and screened against the GP of MARV. Sequencing of 192 selected clones identified clones with distinct VH and VL sequences. Of these 192 selected clones, 18 were ultimately further screened and characterized.

Definitions

By "immunoglobulin" is meant to include neutralizing antibodies as well as fragments thereof. Immunoglobulins can include Fab, Fab', or F(ab')2 fragment, diabodies, bispecific antibodies, and scFv.

By "humanized antibodies" refer to antibodies and immunoglobulins with reduced immunogenicity in humans.

By "chimeric antibodies" refer to antibodies with reduced immunogenicity in humans built by genetically linking a non-human variable region to human constant domains.

By "treat" includes therapeutic treatment, where a condition to be treated is already known to be present (an infection by a Marburg virus) and prophylaxis—i.e., prevention of, or amelioration of an infection by a Marburg virus, the possible future onset of a condition, in this. The infection can be by a Marburg virus strain such as Ci67, Ravn, Angola, Musoke, Uganda 200703648, Angola prototype 20051379, and Angola-810820.

As used herein, a "therapeutically effective" treatment refers a treatment that is capable of producing a desired effect. Such effects include, but are not limited to, enhanced survival, reduction in presence or severity of symptoms, reduced time to recovery, and prevention of initial infection. By an "effective amount" is an amount sufficient to provide protection in a murine model against the Marburg virus infection. In a murine model, and effective amount of an anti-Marburg reactive immunoglobulin would protect the mouse from infection by either the wild type Marburg virus or the mouse adapted virus.

By "antibody" is meant to include a monoclonal antibody (mAb), or an immunologically effective fragment thereof, such as an Fab, Fab', or F(ab')2 fragment thereof. In some contexts, herein, fragments will be mentioned specifically for emphasis; nevertheless, it will be understood that regardless of whether fragments are specified, the term "antibody" includes such fragments as well as single-chain forms. As long as the protein retains the ability specifically to bind its intended target, it is included within the term "antibody." Preferably, but not necessarily, the antibodies useful in the invention are produced recombinantly. Antibodies may or may not be glycosylated, though glycosylated. Antibodies are preferred, especially IgG antibodies. The glycosylated antibodies can contain glycans that are largely devoid of fucose. Alternatively, the glycosylated antibodies contain glycans that are galactosylated. Galactosylated antibodies can contain glycans that are sialylated. Antibodies are properly cross-linked via disulfide bonds, as is well known.

Light chains are classified as kappa (κ) and lambda (λ). A list of preferred heavy and light chain sequences are provided in FIG. 12. Heavy chains are classified as gamma, mu, alpha, delta, or epsilon, and define the antibody's isotype as IgG, IgM, IgA, IgD and IgE, respectively. Within each isotype, there may be subtypes, such as IgG1, IgG2, IgG3, IgG4, etc. Within light and heavy chains, the variable and constant regions are joined by a "J" region of about 12 or more amino acids, with the heavy chain also including a "D" region of about 3 or more amino acids. The particular identity of constant region, the isotype, or subtype does not impact the present invention. The variable regions of each light/heavy chain pair form the antibody binding site.

An intact antibody has two binding sites. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with known conventions (e.g. Kabat "Sequences of Proteins of Immunological Interest" National Institutes of Health, Bethesda, Md., 1987 and 1991; Chothia, et al., *J. Mol. Biol.* 196: 901-917 (1987); Chothia, et al., *Nature* 342: 878-883 (1989)).

An "isolated antibody", as used herein, is intended to refer to an antibody or antibody fragment that is substantially free of other antibodies (Abs) or antibody fragments having different antigenic specificities (e.g., an isolated antibody that specifically binds a strain of Marburg virus). I A "blocking antibody" or a "neutralizing antibody", as used herein (or an "antibody that neutralize Marburg virus activity" or "antagonist antibody"), is intended to refer to an antibody whose binding to Marburg virus results in inhibition of at least one biological activity of Marburg virus. For example, an antibody of the invention may prevent or block Marburg virus attachment to, entry into a host cell, or budding from an infected cell. In addition, a "neutralizing antibody" is one that can neutralize, i.e., prevent, inhibit, reduce, impede or interfere with, the ability of a pathogen to initiate and/or perpetuate an infection in a host. The terms "neutralizing antibody" and "an antibody that neutralizes" or "antibodies that neutralize" are used interchangeably herein. These antibodies can be used, alone or in combination, as prophylactic or therapeutic agents with other anti-viral agents upon appropriate formulation, or in association with active vaccination, or as a diagnostic tool. Examples of such antibodies would contain the heavy and light chain sequences as depicted in FIG. 12.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "cross-competes", as used herein, means an antibody or antigen-binding fragment thereof binds to an antigen and inhibits or blocks the binding of another antibody or antigen-binding fragment thereof. The term also includes competition between two antibodies in both orientations, i.e., a first antibody that binds and blocks binding of second antibody and vice-versa. In certain embodiments, the first antibody and second antibody may bind to the same epitope. Alternatively, the first and second antibodies may bind to different, but overlapping epitopes such that binding of one inhibits or blocks the binding of the second antibody, e.g., via steric hindrance. Cross-competition between antibodies may be measured by methods known in the art, for example, by a real-time, label-free bio-layer interferometry assay.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule. For example, the antibody may have 90% or more sequence identity to the heavy and or light chains depicted in FIG. 12. In the CBR domain, there may be 1 to 2 amino acids substitutions across the 3 light chain CDRs or the 3 heavy chain CDRs.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson, *Methods Mol. Biol.* 24: 307-331 (1994). Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al., *Science* 256: 1443-45 (1992). A "moderately conservative" replacement is any change having a nonnegative value in the PAM250 log-likelihood matrix.

As used herein, the terms "treat", "treating", or "treatment" refer to the reduction or amelioration of the severity of at least one symptom or indication of Marburg virus infection due to the administration of a therapeutic agent such as an antibody or antibody fragment as described herein to a subject in need thereof. The terms include inhibition of progression of disease or of worsening of infection. The terms also include positive prognosis of disease, i.e., the subject may be free of infection or may have reduced or no viral titers upon administration of a therapeutic agent such as an antibody of the present invention. The therapeutic agent may be administered at a therapeutic dose to the subject.

The terms "prevent", "preventing" or "prevention" refer to inhibition of manifestation of Marburg virus infection or any symptoms or indications of Marburg virus infection upon administration of an antibody or antibody fragment as described herein. The term includes prevention of spread of infection in a subject exposed to the virus or at risk of having Marburg virus infection.

As used herein, the term "anti-viral drug" refers to any anti-infective agent or therapy, whether it is a chemical moiety, or a biological therapy, used to treat, prevent, or ameliorate a viral infection in a subject. For example, in the present invention an anti-viral drug may include, but not be limited to, an antibody to Marburg virus (in one embodiment the antibody to Marburg virus may be different than those described herein), a vaccine for Marburg virus, brincidofovir (CMX-001), favipiravir (T-705), BCX-4430, and interferons. In the present invention, the infection to be treated is caused by a Marburg virus.

A "pharmaceutically acceptable carrier" in therapeutic compositions may additionally contain liquids such as water, saline, glycerol and ethanol. Auxiliary substances, such as wetting or emulsifying agents or pH buffering substances, may be present in the compositions provided. The pharmaceutically acceptable carrier should not itself induce the production of antibodies harmful to the individual receiving the composition and should not be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles. Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilizing and/or dispersing agents. Alternatively, the immunoglobulin may be in dry form, for reconstitution before use with an appropriate sterile liquid. Pharmaceutically acceptable salts can be used, for example mineral acid salts, such as hydrochlorides, hydrobromides, phosphates and sulfates, or salts of organic acids, such as acetates, propionates, malonates and benzoates.

Therapeutic Uses of the Antibodies.

The antibodies of the present invention are useful for the treatment, and/or prevention of a disease or disorder or condition associated with Marburg virus infection and/or for ameliorating at least one symptom associated with a Marburg virus infection.

The antibodies can be useful to treat subjects suffering from the severe and acute respiratory infection caused by Marburg virus. One or more antibodies having the heavy and light chains provided in FIG. 12 or variants thereof can be used to decrease or reduce viral titers or viral load in the infected host. An antibody or antigen-binding fragment thereof may be administered at a therapeutic dose to a patient with Marburg virus infection.

One or more antibodies may be administered to relieve or prevent or decrease the severity of one or more of the symptoms or conditions of the Marburg infection. For example, an antibody containing the heavy and light chains of R3F6, R4A1, R4B11, or R4G2 can be used alone or in combination with one or more of the other three. One or more of R3F6, R4A1, R4B11, and R4G2 can be further combined with an additional antibody comprising a light and heavy chain sequence as depicted in FIG. 12. The antibodies may be used to ameliorate or reduce the severity of at least one symptom of Marburg virus infection including, but not limited to fever, headache, fatigue, loss of appetite, myalgia, diarrhea, vomiting, abdominal pain, dehydration and unexplained bleeding.

One or more antibodies can be administered prophylactically to subjects at risk for developing an Marburg virus infection such as an immunocompromised individual, a healthcare worker, a person who is suspected of having been exposed to a person harboring the Marburg virus, a person who comes into physical contact or close physical proximity with an infected individual or animal, sexual contact with an infected or suspected infected individual, hospital employee, a pharmaceutical researcher, maintenance personnel responsible for cleaning a hospital facility or institution where an Marburg infected subject has been treated, individuals who have visited or are planning to visit an area or country known to have or suspected to have an outbreak of Marburg virus or a frequent flyer to countries with a Marburg outbreak. Other exposures wherein prophylactic and/or therapeutic use can be utilized include needle sticks with contaminated needles or potentially contaminated needles along with other laboratory incidents, blood-to-blood transfers or exposure to bodily fluids from infected individuals.

The disclosed antibodies can be used to prepare a pharmaceutical composition for treating patients suffering from a Marburg virus infection. Individual antibodies or combinations of antibodies can be used with an adjunct therapy, e.g., with any other agent or any other therapy known to those skilled in the art useful for treating or ameliorating a Marburg virus infection.

Combination Therapies.

Combination therapies may include an anti-Marburg virus antibody and any additional therapeutic agent including another anti-Marburg virus antibody.

The antibodies of the present invention may be combined synergistically with one or more drugs or agents used to treat or prophylactically prevent a Marburg virus infection.

For example, exemplary agents for treating a viral infection may include, e.g., anti-viral drug, an anti-inflammatory drug (such as corticosteroids, and non-steroidal anti-inflammatory drugs), a different antibody to Marburg virus, a vaccine for Marburg virus, brincidofovir (CMX-001), favipiravir (T-705), BCX-4430, interferons, or any other palliative therapy to treat an Marburg virus infection.

The antibodies described herein may be combined with a second therapeutic agent to reduce the viral load in a patient with a Marburg virus infection, or to ameliorate one or more symptoms of the infection.

A combination of anti-Marburg virus antibodies, wherein the combination comprises one or more antibodies that do not cross-compete can be used. The combination includes a cocktail comprising a mixture of at least three antibodies described herein. The antibodies within the cocktail may differ in their ability to neutralize virus or virus infected cells, or in their ability to mediate antibody-dependent cellular cytotoxicity (ADCC).

As used herein, the term "in combination with" means that additional therapeutically active component(s) may be administered prior to, concurrent with, or after the administration of at least one anti-Marburg virus antibody, or a cocktail comprising one or more of the antibodies disclosed herein. The term "in combination with" also includes sequential or concomitant administration of an anti-Marburg virus antibody and a second therapeutic agent.

The additional therapeutically active component(s) may be administered to a subject prior to administration of an anti-Marburg virus antibody. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. The additional therapeutically active component(s) may be administered to a subject after administration of an anti-Marburg virus antibody.

"Concurrent" administration includes, e.g., administration of an anti-Marburg virus antibody and an additional therapeutically active component to a subject in a single dosage form, or in separate dosage forms administered to the subject within about 30 minutes or less of each other. If administered in separate dosage forms, each dosage form may be administered via the same route (e.g., both the anti-Marburg virus antibody and the additional therapeutically active component may be administered intravenously, etc.); alternatively, each dosage form may be administered via a different route (e.g., the anti-Marburg virus antibody may be administered intravenously (i.v.), and the additional therapeutically active component may be administered orally). The amount of the composition to be administered.

iv. can be from about 2.5 mg/kg to about 100 mg/kg subject weight or 5 mg/kg to about 50 mg/kg body weight. The administration can also be subcutaneous (s.c.) if the composition is in concentrated form. For example, the s.c. dose could be from about 25 to about 200 mg/kg subject weight, or 50 to 150 mg/kg patient weight, or 75 to 150 mg/kg patient weight. In any event, administering the components in a single dosage from, in separate dosage forms by the same route, or in separate dosage forms by different routes are all considered "concurrent administration," for purposes of the present disclosure.

The terms "initial dose," "secondary doses," and "tertiary doses," refer to the temporal sequence of administration of an anti-Marburg virus antibody. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-Marburg virus antibody, but generally may differ from one another in terms of frequency of administration.

In certain exemplary embodiments of the present invention, each secondary and/or tertiary dose is administered 1 to 48 hours after the immediately preceding dose. The phrase "the immediately preceding dose" means in a sequence of multiple administrations, the dose of anti-Marburg virus antibody, which is administered to a patient prior to the administration of the very next dose in the sequence with no intervening doses.

The methods according to this aspect of the invention may comprise administering to a patient any number of secondary and/or tertiary doses of an anti-Marburg virus antibody. For example, only a single secondary dose may need to be administered to the patient. Alternatively, two or more (e.g., 2, 3, 4, 5, 6, 7, 8, or more) secondary doses can be administered to the patient.

The frequency at which the secondary and/or tertiary doses are administered to a patient can vary over the course of the treatment regimen and depends on whether the treatment is for prophylaxis or treatment of an exposure. The frequency of administration may also be adjusted during the course of treatment by a physician depending on the needs of the individual patient.

EXAMPLES

Non-human primates (NHP), cynomolgus macaques, were immunized with viral-replicon particles expressing the glycoproteins (GP) of MARV (Ci67 isolate). An antibody fragment (single chain variable fragment, scFv) phage display library was built after four immunogen injections, and screened against the GP1-649 of MARV. Sequencing of 192 selected clones identified 18 clones with distinct VH and VL sequences. Four of these recombinant antibodies (R4A, R4B11, R4G2, and R3F6) were produced in the scFv-Fc format for in vivo studies. Mice that were challenged with wild-type Marburg virus (Ci67 isolate) receiving 100 µg of scFv-Fc on days −1, 1, and 3 demonstrated protective efficacies ranging from 75-100%. The amino-acid sequences of the scFv-Fcs are similar to those of their human germline counterparts, sharing an identity ranging between 68 and 100% to human germline immunoglobulin. These results demonstrate for the first time that recombinant antibodies offer protection against wild-type MARV, and suggest they may be promising candidates for further therapeutic development especially due to their human homology.

Materials and Methods

Macaque Immunization.

Virus replicon particles (VRPs) on a Venezuelan equine encephalitis virus platform were first developed by Pushko et al. (Pushko P et al., "Recombinant RNA replicons derived from attenuated Venezuelan equine encephalitis virus protect guinea pigs and mice from Ebola hemorrhagic fever virus," *Vaccine* 2000 19(1): 142-53). Filovirus-specific VRPs expressing MARV GP at their surface have been previously shown protection in rodents and NHPs (Hevey M, et al., Marburg virus vaccines based upon alphavirus replicons protect guinea pigs and nonhuman primates," *Virology* 1998 251(1): 28-37). VRPs expressing MARV GP were injected intramuscularly (i.m) into a cynomolgus macaque (*Macaca fascicularis*). The first injection consisted of MARV VRP at a concentration of $9.0 \times 10^8$ VRP/mL. Two additional injections were completed at 30 day intervals followed by a final booster (fourth) injection 88 days after the third injection, all at $9.0 \times 10^8$ VRP/mL.

The macaque immunizations were approved by the Institut de Recherche Biomédicale des Armées Ethics committee (Comité d'éthique de l'Institut de Recherche Biomédicale du Service de Santé des Armées) under authorization no. 2008/03.0 and were performed in accordance with all relevant French laws and ethical guidelines, including, in particular (1) "partie règlementaire du livre II du code rural (Titre I, chapitre IV, section 5, sous-section 3: expérimentation sur l'animal)," (2) "décret 87-848 du 19-10/1987 relatif aux expréiences pratiquées sur les animaux vertébrés modifié par le décret 2001/464 du 29 May 2001," (3) "arrêté du 29 octobre 1990 relatif aux conditions de l'expérimentation animale pour le Ministère de la Défense," and (4) "instruction 844/DEF/DCSSA/AST/VET du 9 avril 1991 relative aux conditions de réalisation de l'expérimentation animale." Animal care procedures complied with the regulations detailed under the Animal Welfare Act and in the Guide for the Care and Use of Laboratory Animals. Animals were kept at a constant temperature (22° C. 2° C.) and relative humidity (50%), with 12 h of artificial light per day. Animals were anesthetized before the collection of blood or bone marrow by an intramuscular injection of 10 mg/kg ketamine (Imalgene®, Merial). If the animal technicians suspected that the animal was in pain, on the basis of their observations of animal behavior, analgesics were subsequently administered, through a single intramuscular injection of 5 mg/kg flunixine (Finadyne®, Schering Plough) in the days after interventions.

Construction and Screening of the Anti-MARV Antibody Gene Library.

RNA from lymphocytes of the macaque bone marrow was prepared with Tri Reagent (Molecular Research Center Inc., Cincinnati, USA). The isolated RNA was reverse transcribed to cDNA using Superscript II and oligo (dT) (Invitrogen, USA). Combinations of forward and reverse primers were used to amplify the regions coding for the variable regions VLK and VH as previously described (Andris-Widhopf J. et al., 3rd. "Generation of human scFv antibody libraries: PCR amplification and assembly of light- and heavy-chain coding sequences," *Cold Spring Harb. Protoc.* 2011 2011(9)). PCR products were cloned in the pGemT vector (Promega, Madison, Wis.) according to the manufacturer's instructions, yielding two sub-libraries encoding the heavy chains (Fd fragment) or the kappa light chains.

The pGemT cloned PCR products were reamplified using two macaque oligonucleotide primer sets to introduce restriction sites for library cloning as described before. Rulker T., et al., "Isolation and characterisation of a human-like antibody fragment (scFv) that inactivates VEEV in vitro and in vivo," PloS one* 2012; 7(5): e37242; Schirrmann T., et al., "Oligomeric forms of single chain immunoglobulin (seIgG)," *mAbs* 2010; 2(1): 73-6; and Schutte M. et al., "Identification of a putative Crf splice variant and generation of recombinant antibodies for the specific detection of *Aspergillus fumigatus," PloS one* 2009 4(8): e6625. In brief, the secondary PCRs were carried out for each forward oligonucleotide primers separately to keep the diversity. Each PCR was performed in a volume of 100 μL using 100 ng purified PCR reaction product of the pGemT cloned cDNA, 2.5 U Go Taq polymerase (Promega, Mannheim, Germany), 200 μM dNTPs each, and 200 nM of each oligonucleotide primer for 20 cycles (30 s at 94° C., 30 s at 57° C., 30 s at 72° C.), followed by 10 min at 72° C. The PCR products were separated by 1.5% (w/v) agarose gel, cut out, and purified using Nucleospin Extract II Kit (Macherey-Nagl, Dren, Germany) according to the manufacturer's instructions.

The construction of the library was completed in two subsequent steps. First, the PCR products encoding VL were cloned into pHAL35. pHAL35 was derived from pHAL14 with an additional SfiI site for VH cloning and Myc-His tag orientation instead of His-Myc (Hust M. et al., "A human scFv antibody generation pipeline for proteome research," *Journal of biotechnology* 2011 152(4): 159-70). Second, the VH PCR fragments were cloned. A total of 5 μg pHAL35 and 2 μg VL were digested using 50 U MluI and 50 U NotI (NEB, Frankfurt, Germany) in a 100 μL reaction volume for 2 h at 37° C. Afterwards, 0.5 U calf intestinal phosphatase (MBI Fermentas) was added and incubated for further 30 min. This dephosphorylation step was repeated once. The vector was purified using the Nucleospin Extract II Kit (Macherey-Nagel, Düren, Germany) according to manufacturer's instructions. 270 ng VL were cloned into 1 g of the dephosphorylated pHAL35 using 1 U ligase (Promega, Mannheim, Germany) overnight at 16° C. The ligation reactions were precipitated with 10 uL of 99.8% ethanol with 3N sodium acetate pH 5.2 and the pellet was washed twice with 70% ethanol. These reactions were electroporated (1.7 kV) in 25 μL XL1-Blue MRF' (Agilent, Böblingen, Germany). The transformed bacteria were plated onto 2×YT agar plates (Sambrook and Russell, 2001) (25 cm Petri dishes) supplemented with 100 μg/mL ampicillin, 20 μg/mL tetracycline, and 100 mM glucose. The colonies were harvested by suspending in 40 mL 2×YT media with a Drigalsky spatula. Plasmids were isolated using the Nucleobond Plasmid Midi Kit (Macherey-Nagel, Düren, Germany) according to the manufacturer's instructions. Afterwards, 5 μg of each VL chain library as well as 2 g of the VH fragments were digested using 50 U HindIII (NEB) in a 100 μL reaction volume overnight at 37° C. followed by 50 U SfiI (NEB) for 2.5 h at 50° C. In total, 4 transformations were performed and pooled. The harvested bacteria representing the final antibody gene libraries were aliquoted and stored at −80° C.

Library Packaging.

400 mL 2×YT medium supplemented with 100 μg/mL ampicillin and 100 mM glucose were inoculated with the library glycerin stock of the pooled library (Sambrook J, D. R. MOLECULAR CLONING: A LABORATORY MANUAL (New York: Cold Spring Harbor Laboratory Press; 2001). The bacteria were grown to O.D.600=0.4-0.5 at 37° C. and 250 rpm. 25 mL bacteria (~1.25×10$^{10}$ bacteria) were infected with 2.5×10$^{11}$ Hyperphage, incubated at 37° C. for 30 min without shaking, followed by 30 min at 250 rpm (Rondot S. et al., "A helper phage to improve single-chain antibody presentation in phage display," *Nature Biotechnology* 2001 19(1): 75-8; and Soltes G., et al., "On the influence of vector design on antibody phage display," *J. Biotechnology* 2007 127(4): 626-37). The infected cells were harvested by centrifugation for 10 min at 3,220×g and the pellet was resuspended in 30 mL 2×YT supplemented with 100 μg/mL ampicillin and 50 μg/mL kanamycin, and cultivated over night at 30° C. and 250 rpm. Bacteria cells were pelleted for 10 min at 10,000× g. Phage particles in the supernatant were precipitated with ⅕ volume of 20% PEG/2.5 M NaCl solution for 1 h on ice with gentle shaking and pelleted 1 h at 10,000×g at 4° C. The precipitated phage were resuspended in 10 mL phage dilution buffer (10 mM Tris.HCl pH7.5, 20 mM NaCl, 2 mM EDTA), sterile filtered using a 0.45 μm filter and precipitated again with ⅕ volume of Polyethylene glycol (PEG) 3350 solution for 20 min on ice, and pelleted 30 min at 10,000×g at 4° C. The precipitated phage were re-suspended in 300 μL PBS (phosphate buffered saline) and cell debris was pelleted by additional centrifugation for 5 min at 15,400×g at 20° C. The supernatant containing the scFv phage were stored at 4° C. The library packaging was analyzed by SDS-PAGE (sodium dodecylsulfite polyacrylamide gel electrophoresis), Western blot, and anti-pIII immunostaining as described before (Frenzel A., et al., "Construction of human antibody gene libraries and selection of antibodies by phage display," *Methods Mol. Biol.* 2014 1060: 215-43). Screening of the library was performed as described elsewhere (Pelat T., et al., "Non-human primate immune libraries combined with germline humanization: an (almost) new, and powerful approach for the isolation of therapeutic antibodies," mAbs 2009 1(4): 377-81), except that 5, 10, 20, and 40 washes were performed for each successive round of panning; MARV GP1-649 was utilized as the antigen and Tris Buffered Saline TBS-Tween20 at 0.1% as the washing buffer.

Sequence Analysis.

A sequence analysis of similarities between macaque VH and VL and the closest human germline genes will newsletter speaking were not interested in encoding VH and VL was performed utilizing the IMGT database (<http://www.imgt.org/IMGTect/>) (Table 1).

TABLE 1

Germline sequence similarity of 18 distinct scFv antibody fragments isolated from panning. Macaque $V_H$ and $V_L$ similarity with their human germline counterparts were calculated.

| | Heavy chain ($V_H$) | | Light chain ($V_L$) | |
|---|---|---|---|---|
| Antibody | Human Germline Family ID | % Identity | Human Germline Family ID | % Identity |
| R4A1 | IGHV3-11*04 | 88.8 | IGKV1-5*01 | 93.6 |
| R4B11 | IGHV1-69*09 | 80.6 | IGKV1D-12*01 | 88.4 |
| R4G2 | IGHV3-23*01 | 60.8 | IGKV1-5*01 | 78.9 |
| R4G7 | IGHV3-23*01 | 77.3 | IGKV1-5*01 | 78.9 |
| R4G8 | IGHV3-23*02 | 76.3 | IGKV1-5*01 | 81.1 |
| R4G9 | IGHV3-23*01 | 79.4 | IGKV1-5*01 | 81.1 |
| R4G10 | IGHV3-23*04 | 61.9 | IGKV1-5*01 | 78.9 |
| R4G11 | IGHV3-23*02 | 75.3 | IGKV1-5*01 | 81.8 |
| R4H11 | IGHV3-23*02 | 75.3 | IGKV1-5*01 | 81.1 |
| R4H12 | IGHV3-23*02 | 76.3 | IGKV1-5*01 | 81.1 |
| R3C4 | IGHV1-69*09 | 84.7 | IGKV1D-12*01 | 85.3 |
| R3D4 | IGHV3-23*02 | 75.3 | IGKV1-5*01 | 81.1 |
| R3F6 | IGHV3-23*01 | 78.4 | IGKV1-5*01 | 80.0 |
| R3G2 | IGHV3-23*02 | 71.1 | IGKV3-15*01 | 80.0 |

TABLE 1-continued Germline sequence similarity of 18 distinct scFv antibody fragments isolated from panning. Macaque $V_H$ and $V_L$ similarity with their human germline counterparts were calculated.

| | Heavy chain ($V_H$) | | Light chain ($V_L$) | |
|---|---|---|---|---|
| Antibody | Human Germline Family ID | % Identity | Human Germline Family ID | % Identity |
| R3G5 | IGHV4-b*02 | 75.8 | IGKV1-39*01 | 85.3 |
| R3H2 | IGHV3-23*02 | 77.3 | IGKV1-5*01 | 81.1 |
| R3H6 | IGHV3-23*02 | 77.3 | IGKV1-5*01 | 80.0 |
| R3H10 | IGHV3-23*01 | 89.7 | IGKV1-5*01 | 80.0 |

Additionally, the degrees of identities between the macaque V regions with their most similar human germline counterparts were calculated with DomainGapAlign (http://www.imgt.org/3Dstructure-DB/cgi/DomainDisplay.cgi). Pelat T., et al., 2009.

Affinity Measurements.

Affinities were measured by surface plasmon resonance (SPR) utilizing a BIAcore-3000 instrument (Biacore, Uppsala, Sweden). The MARV GP1-649 was immobilized at a maximum of 1000 RU on a CM5 chip (BiaCore) via amine coupling according to the manufacturer's instructions. A 30 µL/min flow rate was maintained for the measurement. For each scFv, eight dilutions were prepared in Hepes Buffered Saline (HBS-EP; 0.01 M HEPES pH 7.4; 0.15 M NaCl, 3 mM EDTA, 0.005% v/v Surfactant P20) buffer (Biacore) with elution times greater than 1,000 seconds. Following each dilution, the chip was regenerated with 1.5 M glycine buffer (Biacore) run at 10 µL/min for 50 seconds. For competition BiaCore epitope binding, MARV GP1-649 was immobilized at a maximum of 400 RU on a CM5 chip (BiaCore) as above. Sets of two antibodies were injected in tandem with the second antibody injection just after the maximal saturation of the epitope. Following the second antibody injection, the chip was regenerated with 1.5 M glycine buffer (Biacore) run at 10 µL/min for 50 seconds. This process was completed until all antibodies could be assessed with one another.

ScFv-Fc Production and Purification.

ScFv fragments isolated by antibody-phage display were subcloned into pCSE2.5-mIgG2c-Fc-XP and produced as scFv-Fc (Yumab) in HEK293-6E cells (National Research Council (NRC), Biotechnological Research Institute (BRI), Montreal, Canada) cultured in chemically defined medium F17 (Invitrogen, Life Technologies, Darmstadt, Germany) supplemented with 1 g/L pluronic F68 (Applichem, Darmstadt, Germany), 4 mM L-glutamine (GE Healthcare, Freiburg, Germany), and 25 mg/L G418 (GE Healthcare, Freiburg, Germany), as previously described (Jager V. et al., "High level transient production of recombinant antibodies and antibody fusion proteins in HEK293 cells," BMC Biotechnology 2013 13: 52). The Fc was of murine origin and the scFv-Fc format is equivalent to IgG. For the scFv-Fc production, DNA was used for the transient transfection of 25 mL cultures of HEK293-6E cells in 125 mL Erlenmeyer shake flasks. After 48 hours of culture with shaking at 110 rpm in a Minitron orbital shaker (Infors, Bottmingen, Switzerland) at 37° C., under an atmosphere containing 5% $CO_2$, one volume of culture medium, with a final concentration of 0.5% (w/v) tryptone N1 (TN1, Organotechnie S.A.S., La Courneuve, France) was used for the purification of a scFv, whereas scFv-Fc were purified on a UNOsphere SUPrA column (Biorad, Munich, Germany) with a Profinia apparatus (BioRad, Hercules, Calif., USA), according to the manufacturer's instructions.

Cell Based Neutralization Assay.

Antibody samples, in the scFv format, were titrated in complete MEM (Sigma) supplemented with 10% FBS (fetal bovine serum). Antibody dilutions were added, in decreasing dilutions, to a constant viral titer for 65 PFU (plaque forming unit) per well for a 1 hr incubation at 37° C. Dilutions were plated in triplicate on 6-well plates containing 95-98% confluent Vero E6 cells (American Type Culture Collection, ATCC). After a 1 hr incubation at 37° C., wells were overlaid with 1% agarose in Eagle's Basal medium (EBME; Sigma) with 10% FBS and 0.1% gentamicin and returned to the incubator for 7 days at 37° C. with 5% $CO_2$. On day 7, a 1% agarose secondary overlay containing 4% neutral red was added, and after 1 more day at 37° C., plaques were counted (Moe J. B., et al., "Plaque assay for Ebola virus," J. Clin. Microbiol. 1981 13(4): 791-3).

Western Blot Analysis.

Irradiated MARV antigen (Ci67, Ravn, Angola, and Musoke) was mixed with 4× loading buffer (Life Technologies) and 2-betamercaptoethanol (BioRad). The samples were heated at 70° C. for 10 minutes and 10 µL was loaded on 4-12% Bis-Tris precast gels (Life Technologies). 10 µL of precision plus protein dual color standard (BioRad) was added to the gels as well. The gels were run at 150 V for 90 minutes in 1×MOPS ((3-(N-morpholino)propanesulfonic acid)) running buffer (Life Technologies). The gels were transferred to 0.45 M nitrocellulose membranes (Life Technologies) via the IBLOT. The membranes were blocked with 5% milk (Microbiology) in PBS (phosphate buffered saline) (Sigma) plus 0.02% Tween20 (Sigma Aldrich) (PBST) for 2 hrs at RT on (Applichem, Darmstadt, Germany), 4 mM L-glutamine (GE Healthcare, Freiburg, Germany) and 25 mg/L G418 (GE Healthcare, Freiburg, Germany), as previously described (Jager V. et al., "High level transient production of recombinant antibodies and antibody fusion proteins in HEK293 cells," BMC Biotechnology 2013 13: 52). The Fc was of murine origin and the scFv-Fc format is equivalent to IgG.

For the scFv-Fc production, DNA was used for the transient transfection of 25 mL cultures of HEK293-6E cells (ATCC) in 125 mL Erlenmeyer shake flasks. After 48 hours of culture with shaking at 110 rpm in a Minitron orbital shaker (Infors, Bottmingen, Switzerland) at 37° C., under an atmosphere containing 5% $CO_2$, one volume of culture medium, with a final concentration of 0.5% (w/v) tryptone N1 (TN1, Organotechnie S.A.S., La Courneuve, France) was used for the purification of a scFv, whereas scFv-Fc were purified on a UNOsphere SUPrA column (BioRad, Munich, Germany) with a Profinia apparatus (Biorad, Hercules, Calif., USA), according to the manufacturer's instructions.

Cell Based Neutralization Assay.

Antibody samples, in the scFv format, were titrated in complete MEM (Sigma) supplemented with 10% FBS. Antibody dilutions were added, in decreasing dilutions, to a constant viral titer for 65 PFU per well for a 1 hr incubation at 37° C. Dilutions were plated in triplicate on 6-well plates containing 95-98% confluent Vero E6 cells. After a 1 hr incubation at 37° C., wells were overlaid with 1% agarose in Eagle's Basal medium (EBME; Sigma) with 10% FBS and 0.1% gentamicin (Life Technologies) and returned to the incubator for 7 days. On day 7, a 1% agarose secondary overlay containing 4% neutral red was added and after 1 more day at 37° C., plaques were counted (Moe J. B., et al., "Plaque assay for Ebola virus," *J. Clin. Microbiol.* 1981 13(4): 791-3).

Western Blot Analysis.

Irradiated MARV antigen (Ci67, Ravn, Angola, and Musoke) was mixed with 4× loading buffer (Life Technologies) and 2-betamercaptoethanol (BioRad). The samples were heated at 70° C. for 10 minutes and 10 µL was loaded on 4-12% Bis-Tris precast gels (Life Technologies). 10 µL of precision plus protein dual color standard (BioRad) was added to the gels as well. The gels were run at 150 V for 90 minutes in 1×MOPS running buffer (Life Technologies). The gels were transferred to 0.45 µM nitrocellulose membranes (Life Technologies) via the iBlot (Life Technologies). The membranes were blocked with 5% milk (Microbiology) in PBS (Sigma) plus 0.02% Tween20 (Sigma Aldrich) (PBST) for 2 hrs at room temperature (RT) on shaker. The primary antibodies were added at 1 ug/ml in 10 mL of blocking buffer and incubated for 1 hr at RT on a shaker. The membranes were washed 3× with PBST for 10 minutes each. Secondary antibody horseradish peroxidase goat anti-mouse gamma (Kirkegaard & Perry Labs) was added at a 1:5,000 dilution in blocking buffer for 1 hr at RT on a shaker. The membranes were washed 3× with 10 mL of PBST for 10 minutes. Gels were imaged on a BioRad imager after staining with TMB (Life Technologies).

Murine Protection Study.

Specific pathogen-free 6- to 8-week-old male and female INF α/β receptor knockout (IFNAR-/-) mice were utilized (Jackson Laboratory Bar Harbor, Me.) as a model for filovirus infection. Research was conducted under The Institutional Animal Care and Use Committee (IACUC) approved protocol in compliance with the Animal Welfare Act, Public Health Service (PHS) Policy, and other Federal statutes and regulations relating to animals and experiments involving animals. The facility where this research was conducted is accredited by the Association for Assessment and Accreditation of Laboratory Animal Care, International and adheres to principles stated in the Guide for the Care and Use of Laboratory Animals, National Research Council, 2011.

One hundred micrograms of each antibody was administered intraperitoneally (i.p.) to groups of mice (n=10/gender with n=20/treatment group) as a scFv-Fc fusion, on Days −1, 1, and 3. On Day 0, mice were transferred to a Biosafety Level 4 containment area and challenged by i.p. inoculation utilizing 1000 plaque forming units (PFU) MARV Ci67. Mice were weighed and monitored twice daily upon onset of symptoms and once daily for 28 days post infection.

Pseudovirion Neutralization Assay.

Viral pseudotypes bearing MARV Musoke GP were generated by infecting 293T cells expressing MARV Musoke GP with VSVΔG, as described previously (Takada A., et al., "A system for functional analysis of Ebola virus Glycoprotein," *Proc. Nat'l Acad. Sci. USA* 1997 94(26): 14764-9). Vero cells were maintained at 37° C. and 5% $CO_2$ in high-glucose Dulbecco's modified Eagle medium (DMEM) (Invitrogen Corp., Carlsbad, Calif.) supplemented with 10% fetal bovine serum. For antibody neutralization experiments, pre-titrated amounts of pseudotype VSV-MARV particles (MOI≈1 IU per cell) were incubated with increasing concentrations of test antibody or scFv molecule, starting at 350 nM concentration, at room temp for 1 h, prior to addition to cell monolayers in 96-well plates. Viral infectivities were measured by automated enumeration of eGFP+ cells (infectious units; IU) using a CellInsight CX5 imager (Thermo Fisher) at 12-14 h post-infection. Viral neutralization data were subjected to nonlinear regression analysis to extract EC50 values (4-parameter, variable slope sigmoidal dose-response equation; GraphPad Prism).

Results

Macaque Immunization and Antibody Generation.

Figure 7:
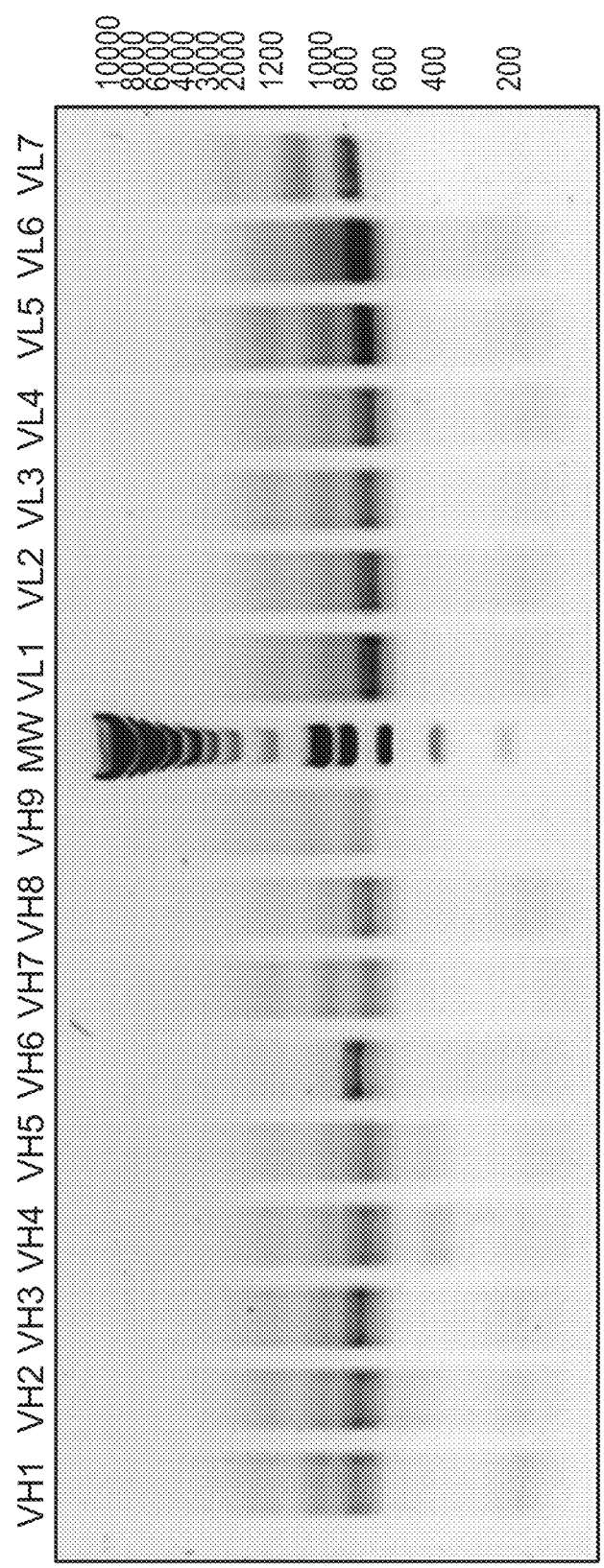
FIG. 7 depicts amplification of VH and VL chains on the eight day following the final injection. Lanes 1-9 show the nine amplified VH families, lane 10 is the molecular weight marker, and lanes 11-17 show the seven amplified VL families.

A single cynomolgus macaque was intramuscularly (i.m.) immunized with four sequential injections of virus replicon particles (VRP) expressing the Marburg GP (isolate Ci67) at surface of cells following viral replication of the complex. The macaque developed increasing anti-GP Ab (antibody) titers as evaluated by ELISA with a titer of 1:316,000 after the second boost and 1:500,000 following the third. (Table S-1) The final boost was given three months after the third injection and eight days later bone marrow samples were harvested. Bone marrow samples were taken on days 3, 6, 8, 12, 18, and 21. The optimal DNA amplification was observed at the day eight time point (FIG. 7 and Tables S 1-3) before the quantity of the amplified variable gene products decreased. The amplified products of VH1 through VH9 and VL1 through VL7 were combined from Day eight collections, and cloned into pGemT for the respective construction of κ light chains and Fd sub-libraries.

TABLE S-1

| | ELISA serum titer response following each successive dose of VRP. | | | |
|---|---|---|---|---|
| N | 1 | 2 | 3 | 4 |
| Days | 0 | 32 | 62 | 150 |
| Dose | 2 × 425 µL at $0.9 \times 10^9$ VRP/mL | 2 × 410 µL at $0.9 \times 10^9$ VRP/mL | 2 × 400 µL at $0.9 \times 10^9$ VRP/mL | 2 × 400 µL at $0.9 \times 10^9$ VRP/mL |
| ELISA Titer (GP) | NT | >1/316,000 | 1/500,000 | NT |
| ELISA Titer (live virus) | NT | >1/316,000 | 1/450,000 | NT |

TABLE S-2

| | RNA extraction quantities following successive bone marrow sampling. | | | | | | |
|---|---|---|---|---|---|---|---|
| | Days from start | | | | | | |
| | 149 | 153 | 156 | 158 | 162 | 168 | 171 |
| Dave sampling | greatest | D 3 | D 6 | D 8 | D 12 | D 18 | D 21 |
| RNA isolated* | 0.25 mg | 0.167 mg | 0.258 mg | 0.225 mg | 0.338 mg | 0.200 mg | 0.189 mg |

*RNA samples are reflected as solid recovery. Generally, each sample is in 200 µL of $ddH_2O$.

TABLE S-3 heavy and light chain amplification by RT PCR.

| | Date from Start | | | | | |
|---|---|---|---|---|---|---|
| | 149 | 153 | 156 | 158 | 162 | 168 |
| | Day of Sampling | | | | | |
| | Pre-Boost | D 3 | D 6 | D 8 | D 12 | D 18 |
| Lk amplified families (− to +++) | | | | | | |
| Vk1 | − | − | ++ | +++ | +++ | +++ |
| Vk2 | − | + | ++ | +++ | +++ | +++ |
| Vk3 | − | − | ++ | +++ | +++ | ++ |
| Vk4 | − | − | ++ | +++ | +++ | +++ |
| Vk5 | − | − | ++ | +++ | ++ | +++ |
| Vk6 | + | + | ++ | +++ | +++ | +++ |
| Vk7 | + | + | ++ | +++ | +++ | +++ |
| H amplified families (− to +++) | | | | | | |
| VH1 | + | + | ++ | +++ | ++ | + |
| VH2 | − | + | + | +++ | + | + |
| VH3 | − | + | + | +++ | ++ | ++ |
| VH4 | − | − | ++ | ++ | ++ | ++ |
| VH5 | − | − | − | +++ | + | + |
| VH6 | − | − | − | +++ | + | + |
| VH7 | + | + | + | +++ | ++ | + |
| VH8 | + | + | + | +++ | ++ | ++ |
| VH9 | − | − | − | ++ | + | + |

Library Construction and Isolation of scFvs Specific to MARV-GP.

For the construction of the immune library, the pGEM-T cloned V-Genes were amplified and cloned into pHAL35 in two subsequent steps. First the VL repertoire was clones and afterwards the VH repertoire, resulting in a library size of $6.04 \times 10^8$ independent clones.

The antibody selection using the generated anti-MARV immune library was performed on MARV Ci67 GP1-649 immobilized in microtiter plates. Four panning rounds were performed with increased stringency. Here, 5, 10, 20, respectively 40 washing steps were performed after each panning round as discussed supra in the section entitled "Library packaging". Finally, $3 \times 10^7$ antibody phage were eluted after the fourth panning round. Subsequently, 194 clones were sequenced and analyzed resulting in eighteen unique antibody sequences (Table 1). The overall identity of the macaque VH and VL sequences with their human germline counterparts averaged 76.7% for VH and 82.1% for VL.

Antibody recovery and characterization. Each of the 18 distinct scFv recovered from the library was assessed for its binding capacity with MARV Ci67 GP1-649 by surface plasmon resonance (SPR). (Table 2) The affinities of the anti-MARV scFv were evaluated under standard conditions, using 800 second elution steps in HBS-EP buffer (FIG. 2), and resulting values ranged from 155 nM for R3H2 to 0.14 nM for R3F6 (Table 2). Of note, R3G5 was unable to produce sufficient quantities of antibody to be further tested.

TABLE 2 antibody affinities as measured by BiaCore with epitope groping.

| Antibody Fragment | $k_{on}$ $M^{-1}s^{-1}$ | $k_{off}$ $s^{-1}$ | $K_D$ (nM) | Epitope Group |
|---|---|---|---|---|
| R4A1 | $6.42 \times 10^4$ | $2.85 \times 10^{-4}$ | 4.4 | 2 |
| R4B11 | $8.76 \times 10^4$ | $4.07 \times 10^{-4}$ | 4.6 | 1 |
| R4G2 | $1.19 \times 10^4$ | $4.54 \times 10^{-4}$ | 38 | 2 |
| R4G7 | $8.19 \times 10^4$ | $3.79 \times 10^{-4}$ | 4.6 | 1 |
| R4G8 | $9.23 \times 10^4$ | $6.3 \times 10^{-3}$ | 68 | 3 |
| R4G9 | $3.1 \times 10^4$ | $1.75 \times 10^{-4}$ | 5.6 | 3 |
| R4G10 | $1.39 \times 10^4$ | $7.46 \times 10^{-4}$ | 54 | 2 |
| R4G11 | $7.5 \times 10^4$ | $4.75 \times 10^{-4}$ | 6.3 | 2 |
| R4H11 | $3.75 \times 10^4$ | $4.17 \times 10^{-4}$ | 11 | 1 |
| R4H12 | $1.46 \times 10^5$ | $5.65 \times 10^{-4}$ | 3.9 | 2 |
| R3C4 | $1.16 \times 10^4$ | $3.86 \times 10^{-4}$ | 33 | ND |
| R3D4 | $1.75 \times 10^4$ | $8.98 \times 10^{-4}$ | 5.1 | 1 |
| R3F6 | $1.99 \times 10^5$ | $2.35 \times 10^{-5}$ | 0.14 | 1 |
| R3G2 | $8.3 \times 10^3$ | $5.78 \times 10^{-4}$ | 69.7 | 2 |
| R3H2 | $6.39 \times 10^3$ | $9.93 \times 10^{-4}$ | 155.0 | 2 |
| R3H6 | $1.74 \times 10^4$ | $5.61 \times 10^{-4}$ | 32.3 | 2 |
| R3H10 | $4.13 \times 10^4$ | $2.83 \times 10^{-4}$ | 6.9 | 2 |

Figure 3:
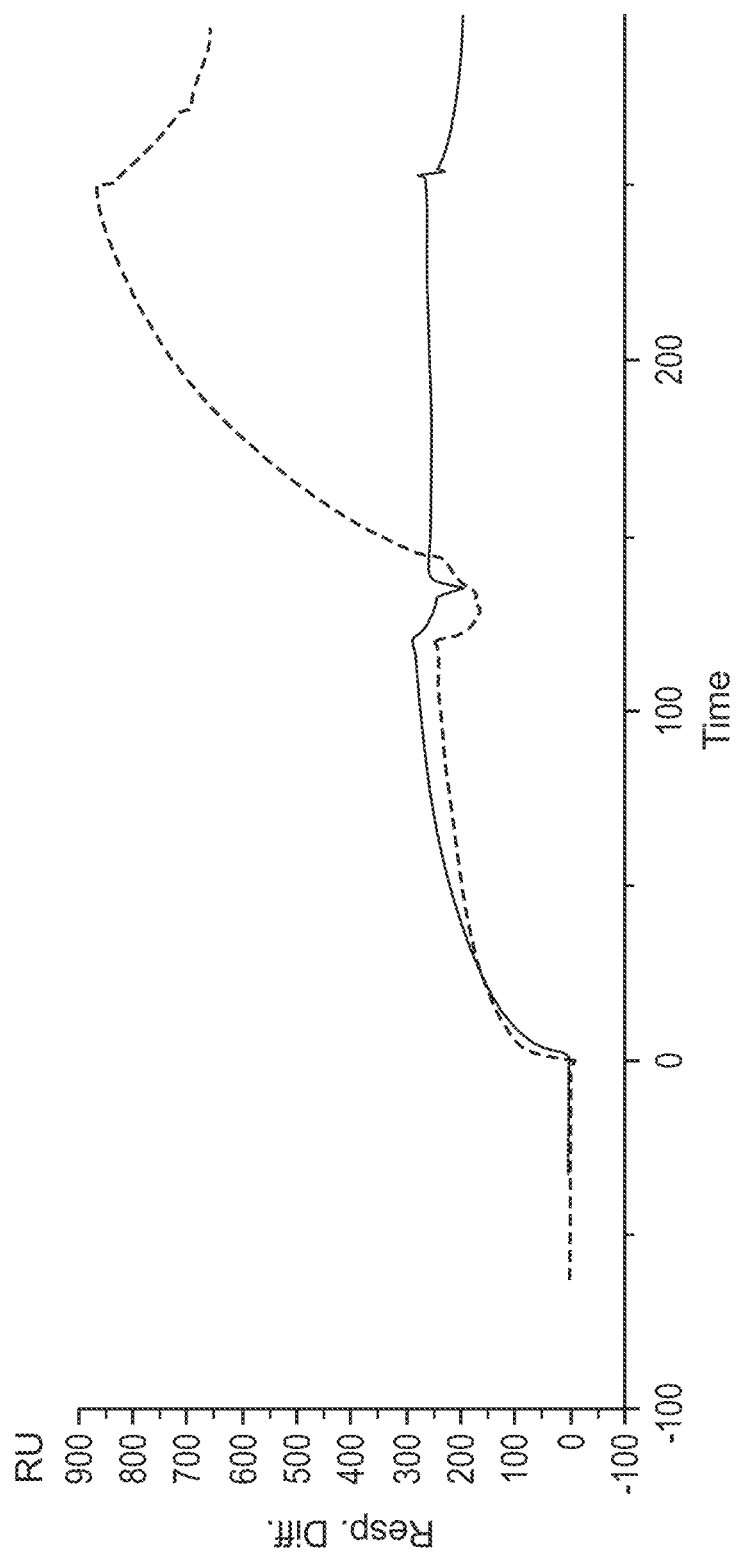
FIG. 3 BiaCore sensorgram of binding analysis between two competitive scFv antibodies (solid line) and two non-competitive scFv antibodies (dashed line).

Classical epitope determination methods utilizing peptide arrays were not successful. To characterize these antibodies, we determined competition groups and isolated specific epitopic families within the 17 remaining antibodies using BiaCore analysis. SM5 chips (BiaCore) were coated with GP1-649 and were pairwise added for sequentially assessment by BiaCore according to manufacturer's instructions. As an example, competitive antibodies had no change in signal (FIG. 3, solid line), while antibodies biding to a new epitope had an increased signal above the first set. (FIG. 3, dashed line). Using this analysis, we identified three distinct groupings of antibodies which were non-competitive (Table 2). The antibody R3C4 is not determined (ND), because its dissociation rate was too rapid to determine a competition grouping.

Four antibodies from the groups above were chosen based on their high affinity to GP1-649, sequence homology, and growth characteristics (data not shown). These antibodies were produced in the scFv-Fc format to assess for cross binding by Western blot analysis as well as for use in protection studies. The selected antibodies were assessed by Western blot analysis; demonstrating cross reactivity to the MARV isolates Ci67, Musoke, and Angola, but with no reactivity to Ravn virus (FIG. 4). Of the four antibodies assessed, all bound strongly to Ci67; R4A1, R4B11, and R3F6 bound strongly to Musoke; and only one of the antibodies, R3F6, demonstrated moderate binding to the Angola isolate.

In Vitro Antibody Neutralization.

The identification of neutralizing mAbs to MARV has been problematic, with neutralizers reported in the literature limited to VSV (vesicular stomatitis virus) expressed Ravn (Fusco M. L., et al., "Protective mAbs and Cross-Reactive mAbs Raised by Immunization with Engineered Marburg Virus GPs," PLoS pathogens 2015; 11(6): e1005016) or Uganda (Flyak A I, et al., "Mechanism of human antibody-mediated neutralization of Marburg virus," Cell 2015; 160 (5): 893-903) glycoprotein, although Kajihara et al. was able to demonstrate an inhibitory mechanism specific to viral budding (Kajihara M., Marzi A., Nakayama E., et al., "Inhibition of Marburg virus budding by nonneutralizing antibodies to the envelope glycoprotein," J. Virology 2012 86(24): 13467-74).

Figure 8:
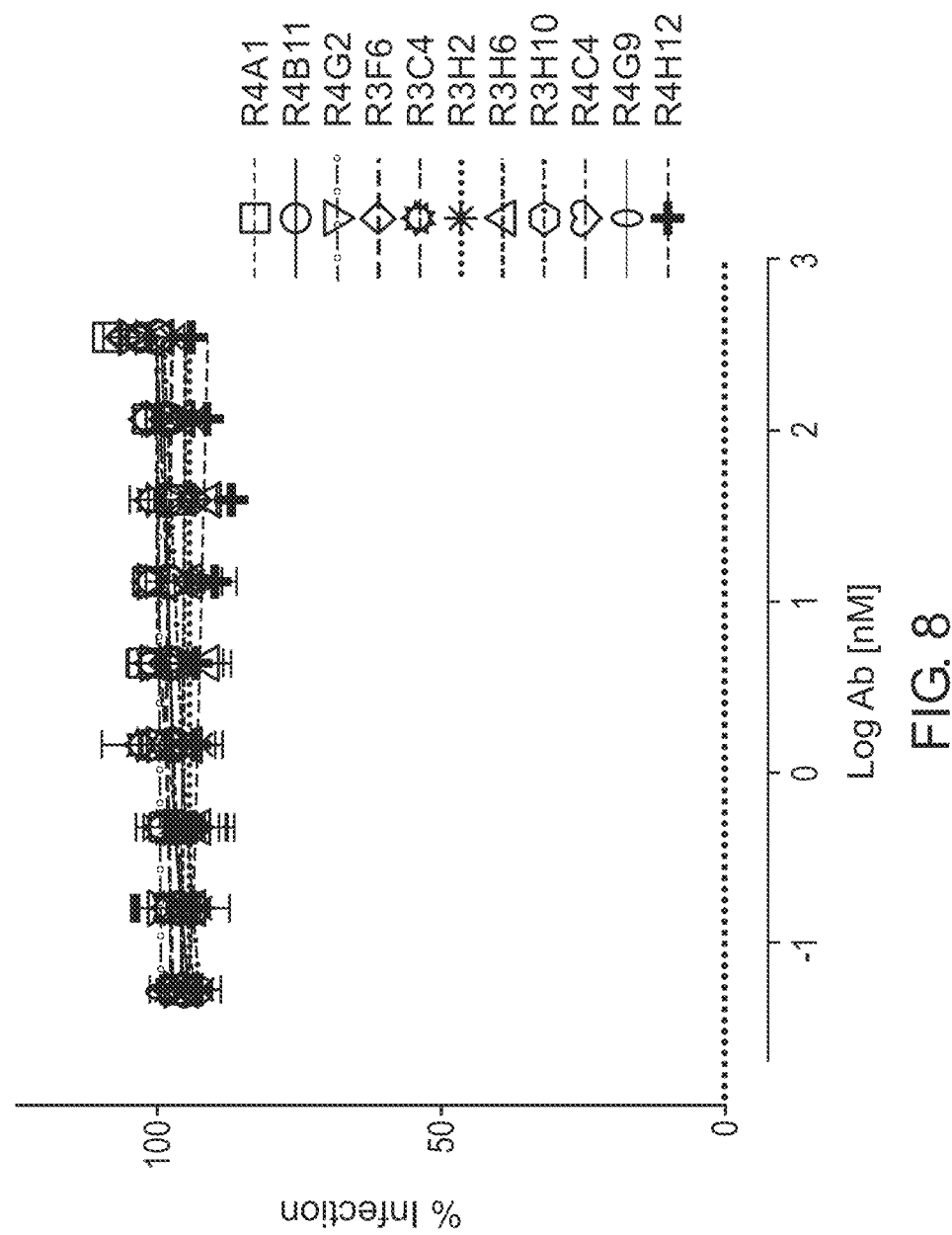
FIG. 8 depicts a pseudovirion neutralization assay of scFv antibodies.

Here, two separate assays to evaluate for neutralization to MARV. ScFv's for 17 of the antibodies (R3C4 was not assessed due to low expression) were tested in a VSV pseudovirion assay expressing the Musoke variant of GP (FIG. 8) as well as the classical plaque reduction neutralization test (PRNT) assay utilizing Ci67 isolate of wild-type MARV. In both of these assays, no antibody reached a PRNT titer of 80% inhibitory concentration. In the classical neutralization assay which measures the ability of a molecule to block viral entry to the cell, plaque sizes appeared as smaller "pinpoint" plaques, and often took an extra day to detect but failed to reach a PRNT titer of 80%. (FIG. 5A). The reduction of these plaque sizes were significant for four of the antibody fragments tested, R3F6, R4A1, R4B11, and R4G2. (FIGS. 5A and B).

In Vivo Mouse Protection Study.

To investigate the in vivo protection of the four selected candidates (R4A1, R4B11, R4G2 and R3F6), each of them was reformatted as scFv-Fc and tested in INF α/β receptor knockout mice (IFNAR–/–; Jackson Laboratory, Maine) challenged with wild-type MARV Ci67. Standard mouse models, using C57BL/6 or BALB/c mice, could only be utilized with a mouse adapted Ravn (Warfield K L, et al., "Development and characterization of a mouse model for Marburg hemorrhagic fever," *J. Virol.* 2009; 83(13): 6404-15) or mouse adapted Ci67 (Flyak A I, et al., "Mechanism of human antibody-mediated neutralization of Marburg virus," *Cell* 2015 160(5): 893-903), as previously done by others.

Figure 6:
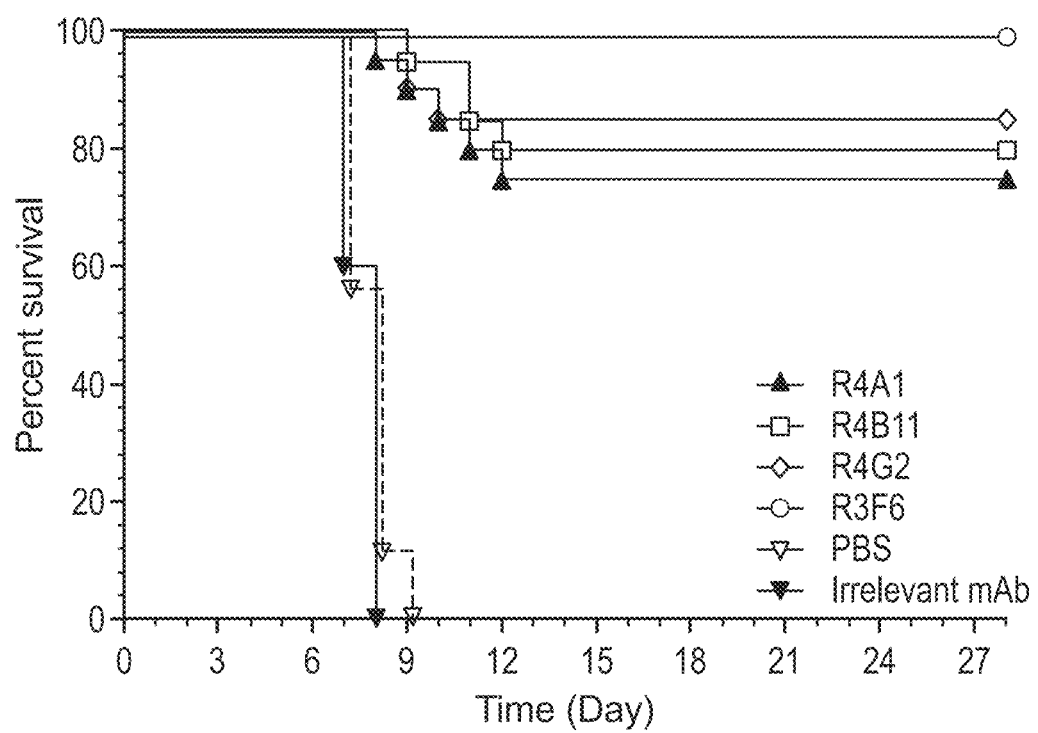
FIG. 6 depicts percent survival of IFNAR−/− mice administered MARV GP specific scFv-Fc antibodies. Each mouse was administered 100 ug of scFv-Fc antibody treatment, irrelevant antibody (n=10), or PBS (n=10) on Days −1, 1, and 3. Mice were challenged with 1000 PFU MARV Ci67 on DO.

All scFv-Fc antibodies synthesized and discussed herein were protective against a lethal MARV Ci67 challenge of 1000 PFU (FIG. 6). The antibody R3F6 demonstrated the best efficacy with 100% protection, under the tested conditions, while R4A1, R4B11, and R4G2 had protective efficacies of 75%, 80%, and 85%, respectively. The protective efficacy at the indicated dose range was similar to that reported in previous studies. Fusco et al. demonstrated post-exposure prophylactic protection using 500 μg of antibody administered 1 hr after 1000 PFU challenge with mouse-adapted Ravn (Fusco M. L., et al., "Protective mAbs and Cross-Reactive mAbs Raised by Immunization with Engineered Marburg Virus GPs," *PLoS pathogens* 2015; 11(6): e1005016.). Flyak et al. preformed a similar approach to our experimental design but with intramuscular administration of a 100 μg of antibody with multi-dose regimen beginning 24-hr pre-exposure followed by 24 hr post-exposure against 1000 PFU mouse-adapted Ci67 strain (Flyak A I, et al., "Mechanism of human antibody-mediated neutralization of Marburg virus," *Cell* 2015; 160(5): 893-903).

Figure 9:
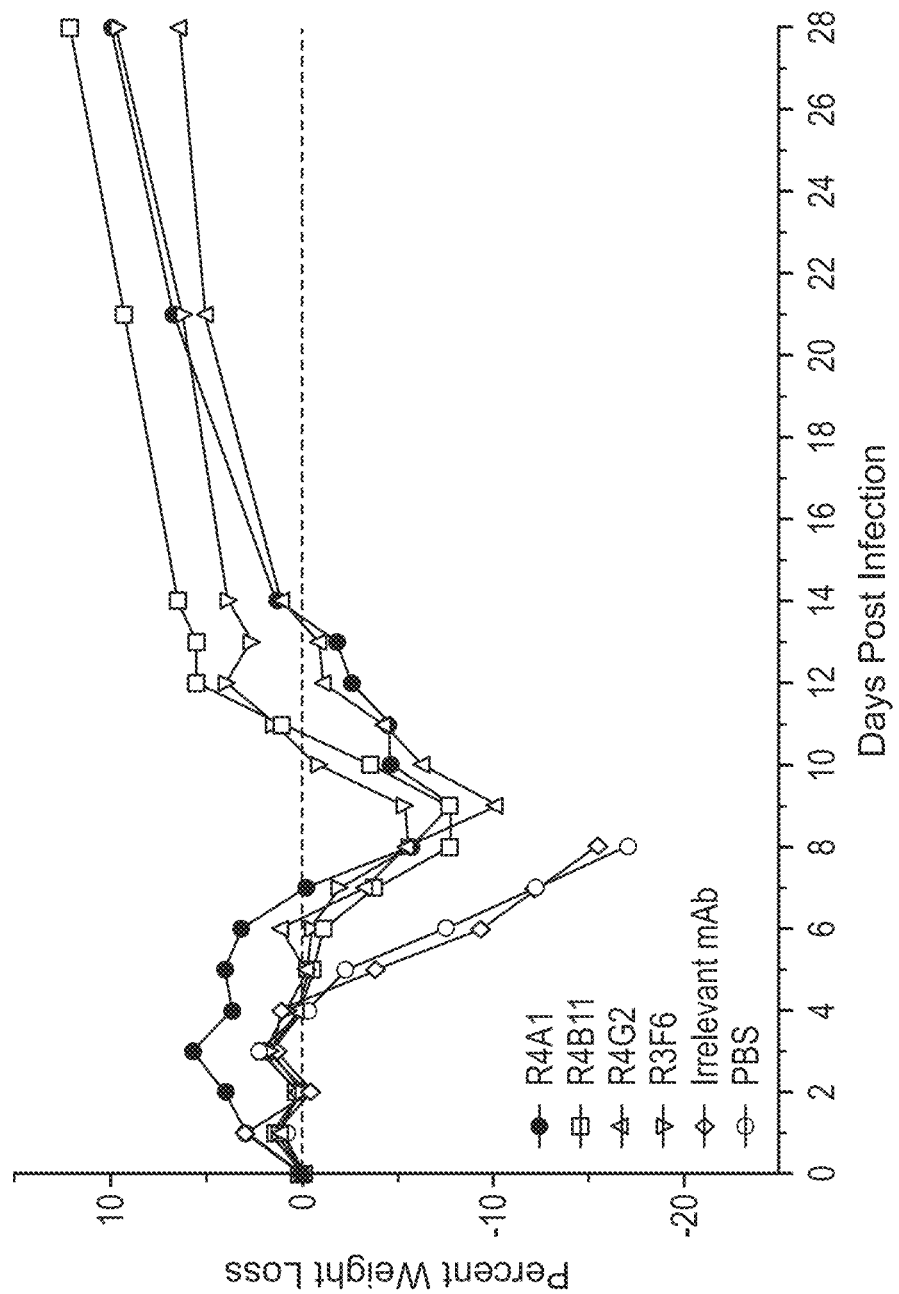
FIG. 9 depicts weight loss in IFNAR−/− mice administered MARV GP specific scFv-Fc antibodies. Each mouse (n=20 per group) was administered 100 g of scFv-Fc antibody, irrelevant antibody (n=10), or PBS (n=10) on Days −1, 1, and 3. Mice were challenged with 1000 pfu MARV C167 on DO.
Figure 10:
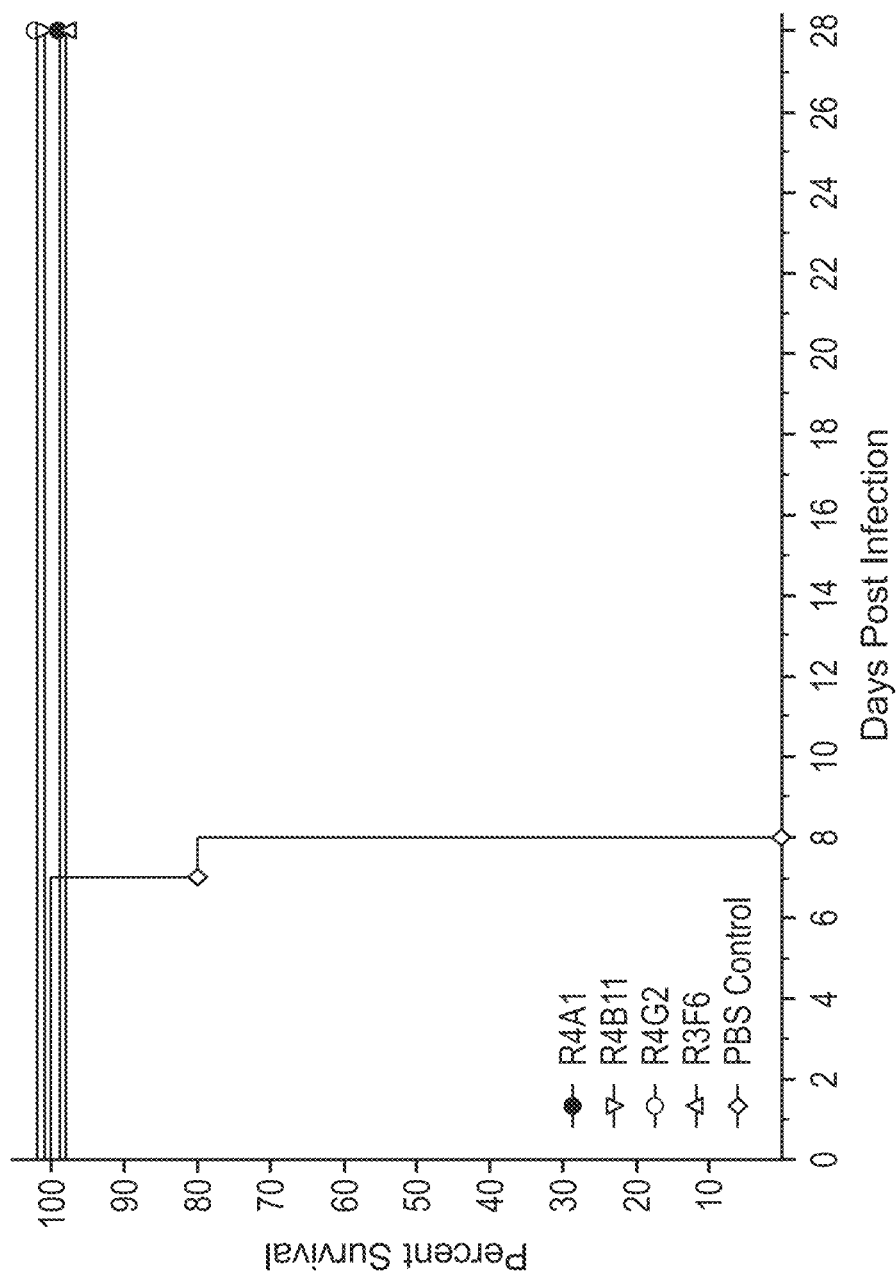
FIG. 10 depicts percent survival following the re-challenge of IFNAR−/− mice administered MARV GP specific scFv-Fc antibodies. Each mouse (n=10 per group or n=5 for the PBS control) was re-challenged with 1000 pfu MARV Ci67 on D35 of the original study, DO indicated above.
Figure 11:
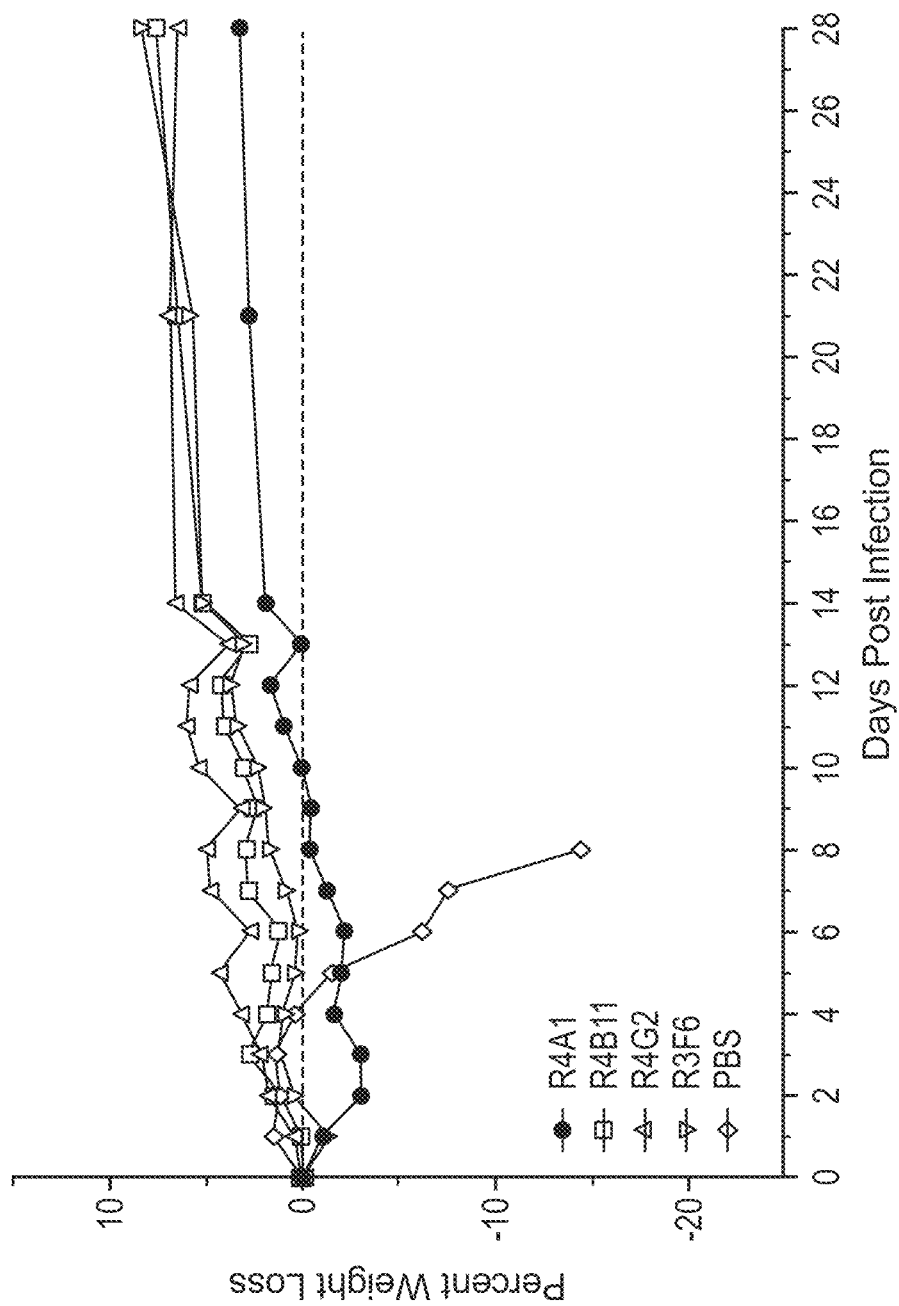
FIG. 11 depicts weight loss following the re-challenge of IFNAR−/− mice administered MARV GP specific scFv-Fc antibodies. Each mouse (n=10 per antibody group or n=5 for the PBS control) was re-challenged with 1000 pfu MARV Ci67 on D35 of the original study, DO indicated above.

The mAbs described herein were assessed in both male and female groups of mice with no efficacy differences observed between genders. In addition to the baseline protection study, the mice were re-challenged thirty-five days after the initial exposure. Surviving mice were challenged with a second injection of 1000 PFU by i.p. with no antibody treatment given. All mice survived the second challenge with no loss in weight, demonstrating that these mice were able to develop a protective memory immune response. (FIG. 9-11)

Discussion.

Previous studies have demonstrated that post-exposure polyclonal antibodies and recombinant monoclonal antibodies may provide protection against filoviruses in Non-Human Primate (NHP) models. There is no clear path for the down selection of antibodies; we chose an approach which identified high binding affinity to the antigen, sequence homology, production capacity and finally protection. Previous work has identified that neutralization may not be the result of higher affinity (Frenzel A., et al., "Construction of human antibody gene libraries and selection of antibodies by phage display," *Methods Mol. Biol.* 2014 1060: 215-43). This gap in the understanding initial in vitro characteristics to protection could be one reason that few monoclonal antibodies have advanced to protection studies. The observation of reduced plaque size in non-neutralizing filovirus mAbs has not been previously reported. Parallels of reduced plaque size has been shown with therapeutics and vaccines to Dengue virus and could indicate that these antibodies are able to inhibit spread of this virus in vitro (Goh K. C., et al., "Molecular determinants of plaque size as an indicator of dengue virus attenuation," *Scientific Reports* 2016 6: 26100.). The decreased plaque size observed herein suggests a blockage of viral spread. There are no reports that identify mAb's protection against wild-type MARV infection. Previous studies have proposed that the protection of MARV may proceed by a mechanism other than the classical mechanism which blocks virus entry (Dye J. M., et al., "Postexposure antibody prophylaxis protects nonhuman primates from filovirus disease," *Proc. Nat'l Acad. Sci. USA* 2012 109(13): 5034-9). It has been shown that antibodies can inhibit the virus by a separate mechanism, viral budding (Kajihara M. et al., "Inhibition of Marburg virus budding by nonneutralizing antibodies to the envelope glycoprotein," *J. Virology* 2012 86(24): 13467-74). These are the first monoclonal antibodies developed from NHP immune libraries utilizing the scFv and scFv-Fc format that provide protection in an animal model for MARV. Although these mAbs were produced and characterized in the scFv and scFv-Fc formats to allow for rapid down selection and identification of lead candidates, it is reasonably expected that the effector functionality and protection of these candidates should be maintained in an IgG format.

Although having both vaccines and pre-exposure therapeutics against viral hemorrhagic fevers would be optimal, the reality is that viral diseases can occur in areas that were not previously known to have a history of that disease or strain so that a vaccination campaign would not be easy to implement. This occurred in 2014 with the EBOV (Ebola virus) outbreak in western Africa, demonstrating that the emergence of a virus could present itself in a population unvaccinated or prepared for such an epidemic. Given the long half-life of human antibodies, approximately 20 days (Brekke O. H., et al., "Therapeutic antibodies for human diseases at the dawn of the twenty-first century," *Nature Rev. Drug Discovery* 2003 2(1): 52-62), a pre-treatment of a protective antibody or cocktail of antibodies can be administered in a prophylactic regimen to population exposed to a virus or in danger of being exposed to a virus. This prophylactic treatment can provide sufficient protection for a significant duration based on the antibody pharmacokinetics, with titers possibly similar to or possibly higher than those provided by a rapid vaccine programs. Furthermore, providing these antibodies would afford immediate protection to an individual while an immunological response is still developing in a vaccinated subject. These antibodies should represent effective pre- and post-exposure treatments.

REFERENCES

1. Kuhn R J. Togaviridae: The Viruses and Their Replication. In: KNIPE D M, HOWLEY P M, EDS. FIELDS VIROLOGY. 5th ed. Philadelphia: Lippincott Williams & Wilkins 2007: 1001-22.
2. MacNeil A, Rollin P E, "Ebola and Marburg hemorrhagic fevers: neglected tropical diseases? *PLoS neglected tropical diseases* 2012; 6(6): e1546.
3. Martini G, Siegert R. Marburg Virus Disease. In: Martini G A, GSiegert R, editors. Marburg virus disease—Congresses Springer-Verlag; 1971. p. 250.
4. Edwards T, Semple M G, De Weggheleire A, et al. Design and analysis considerations in the Ebola_Tx trial evaluating convalescent plasma in the treatment of Ebola virus disease in Guinea during the 2014-2015 outbreak. *Clinical trials* 2016; 13(1): 13-21.
5. Froude J W, Stiles B, Pelat T, Thullier P. Antibodies for biodefense. *mAbs* 2011; 3(6): 517-27.
6. Bradfute S B, Dye J M, Jr., Bavari S. Filovirus vaccines. *Human vaccines* 2011; 7(6): 701-11.
7. Marzi A, Feldmann H. Ebola virus vaccines: an overview of current approaches. *Expert review of vaccines* 2014; 13(4): 521-31.
8. Henao-Restrepo A M, Camacho A, Longini I M, et al. Efficacy and effectiveness of an rVSV-vectored vaccine in preventing Ebola virus disease: final results from the Guinea ring vaccination, open-label, cluster-randomised trial (Ebola Ca Suffit!). *Lancet* 2017; 389(10068): 505-18.
9. Geisbert T W, Pushko P, Anderson K, Smith J, Davis K J, Jahrling P B. Evaluation in nonhuman primates of vaccines against Ebola virus. *Emerging infectious diseases* 2002; 8(5): 503-7.
10. Lupton H W, Lambert R D, Bumgardner D L, Moe J B, Eddy G A. Inactivated vaccine for Ebola virus efficacious in guineapig model. *Lancet* 1980; 2(8207): 1294-5.
11. Sullivan N J, Sanchez A, Rollin P E, Yang Z Y, Nabel G J. Development of a preventive vaccine for Ebola virus infection in primates. *Nature* 2000; 408(6812): 605-9.
12. Swenson D L, Warfield K L, Negley D L, Schmaljohn A, Aman M J, Bavari S. Viruslike particles exhibit potential as a pan-filovirus vaccine for both Ebola and Marburg viral infections. *Vaccine* 2005; 23(23): 3033-42.
13. Mupapa K, Massamba M, Kibadi K, et al. Treatment of Ebola hemorrhagic fever with blood transfusions from convalescent patients. International Scientific and Technical Committee. *The Journal of Infectious Diseases* 1999; 179 Suppl. 1: S18-23.
14. Oswald W B, Geisbert T W, Davis K J, et al. Neutralizing antibody fails to impact the course of Ebola virus infection in monkeys. *PLoS pathogens* 2007; 3(1): e9.
15. Parren P W, Geisbert T W, Maruyama T, Jahrling P B, Burton D R. Pre- and postexposure prophylaxis of Ebola virus infection in an animal model by passive transfer of a neutralizing human antibody. *Journal of virology* 2002; 76(12): 6408-12.
16. Dye J M, Herbert A S, Kuehne A I, et al. Postexposure antibody prophylaxis protects nonhuman primates from filovirus disease. *Proceedings of the National Academy of Sciences of the United States of America* 2012; 109(13): 5034-9.
17. Fusco M L, Hashiguchi T, Cassan R, et al. Protective mAbs and Cross-Reactive mAbs Raised by Immunization with Engineered Marburg Virus GPs. *PLoS pathogens* 2015; 11(6): e1005016.
18. Kajihara M, Marzi A, Nakayama E, et al. Inhibition of Marburg virus budding by nonneutralizing antibodies to the envelope glycoprotein. *Journal of virology* 2012; 86(24): 13467-74.
19. Warfield K L, Bradfute S B, Wells J, et al. Development and characterization of a mouse model for Marburg hemorrhagic fever. *J Virol* 2009; 83(13): 6404-15.
20. Fusco M L, Hashiguchi T, Cassan R, et al. Protective mAbs and Cross-Reactive mAbs Raised by Immunization with Engineered Marburg Virus GPs. *PLoS pathogens* 2015; 11(6): e1005016.
21. Flyak A I, Ilinykh P A, Murin C D, et al. Mechanism of human antibody-mediated neutralization of Marburg virus. *Cell* 2015; 160(5): 893-903.
22. Frenzel A, Kugler J, Wilke S, Schirrmann T, Hust M. Construction of human antibody gene libraries and selection of antibodies by phage display. *Methods Mol Biol* 2014; 1060: 215-43.
23. Goh K C, Tang C K, Norton D C, et al. Molecular determinants of plaque size as an indicator of dengue virus attenuation. *Scientific reports* 2016; 6: 26100.
24. Brekke O H, Sandlie I. Therapeutic antibodies for human diseases at the dawn of the twenty-first century. *Nature reviews Drug discovery* 2003; 2(1): 52-62.
25. Pushko P, Bray M, Ludwig G V, et al. Recombinant RNA replicons derived from attenuated Venezuelan equine encephalitis virus protect guinea pigs and mice from Ebola hemorrhagic fever virus. *Vaccine* 2000; 19(1): 142-53.
26. Hevey M, Negley D, Pushko P, Smith J, Schmaljohn A. Marburg virus vaccines based upon alphavirus replicons protect guinea pigs and nonhuman primates. *Virology* 1998; 251(1): 28-37.
27. Andris-Widhopf J, Steinberger P, Fuller R, Rader C, Barbas C F, 3rd. Generation of human scFv antibody libraries: PCR amplification and assembly of light- and heavy-chain coding sequences. *Cold Spring Harb Protoc* 2011; 2011(9).
28. Rulker T, Voss L, Thullier P, et al. Isolation and characterisation of a human-like antibody fragment (scFv) that inactivates VEEV in vitro and in vivo. *PloS one* 2012; 7(5): e37242.
29. Schirrmann T, Menzel C, Hust M, Prilop J, Jostock T, Dubel S. Oligomeric forms of single chain immunoglobulin (scIgG). *mAbs* 2010; 2(1): 73-6.
30. Schutte M, Thullier P, Pelat T, et al. Identification of a putative Crf splice variant and generation of recombinant antibodies for the specific detection of *Aspergillus fumigatus*. *PloS one* 2009; 4(8): e6625.
31. Hust M, Meyer T, Voedisch B, et al. A human scFv antibody generation pipeline for proteome research. *Journal of biotechnology* 2011; 152(4): 159-70.
32. Sambrook J, D. R. Molecular cloning: a laboratory manual. New York: Cold Spring Harbor Laboratory Press; 2001. antibody presentation in phage display. *Nature biotechnology* 2001; 19(1): 75-8.
34. Soltes G, Hust M, Ng K K, et al. On the influence of vector design on antibody phage display. *Journal of biotechnology* 2007; 127(4): 626-37.
35. Pelat T, Thullier P. Non-human primate immune libraries combined with germline humanization: an (almost) new, and powerful approach for the isolation of therapeutic antibodies. *mAbs* 2009; 1(4): 377-81.
36. Jager V, Bussow K, Wagner A, et al. High level transient production of recombinant antibodies and antibody fusion proteins in HEK293 cells. *BMC biotechnology* 2013; 13: 52.
37. Moe J B, Lambert R D, Lupton H W. Plaque assay for Ebola virus. *J Clin. Microbiol.* 1981; 13(4):791-3.
38. Takada A, Robison C, Goto H, et al. A system for functional analysis of Ebola virus glycoprotein. *Proceedings of the National Academy of Sciences of the United States of America* 1997; 94(26): 14764-9.

SEQUENCE LISTING

<160> NUMBER OF SEQ ID NOS: 36

<210> SEQ ID NO 1
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Leu Glu Ser Gly Gly Asp Leu Val Gln Pro Gly Glu
1               5                   10                  15

Ser Leu Arg Leu Ser Cys Val Ala Ser Gly Ile Ser Phe Ser Asn His
            20                  25                  30

Gly Met Thr Trp Val Arg Gln Ala Pro Gly Lys Gly Leu Asp Trp Val
        35                  40                  45

Ser Ser Ile Asp Ser Asp Gly Gly Thr Phe Tyr Ala Asp Ser Val
    50                  55                  60

Lys Gly Arg Phe Thr Ile Ser Arg Asp Asn Ser Asn Asn Thr Val Ser
65                  70                  75                  80

Leu Gln Met Asn Ser Leu Arg Ala Glu Asp Thr Ala Val Tyr Phe Cys
                85                  90                  95

Ala Ala Arg His Glu Tyr Ser Asp Tyr Tyr Trp Gly Gln Gly Val Leu
            100                 105                 110

Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Ile Glu Leu Thr Gln Ser Pro Ser Thr Leu Ser Val Ser Pro Gly
1               5                   10                  15

Glu Lys Ala Thr Leu Ser Cys Arg Ala Ser Gln Ser Val Gly Ser Arg
            20                  25                  30

Leu Ala Trp Tyr His Gln Ser Pro Gly Gln Ala Pro Arg Leu Leu Ile
        35                  40                  45

Tyr Gly Ala Ser Ser Arg Pro Thr Gly Ile Pro Asp Arg Phe Ser Ala
    50                  55                  60

Ser Gly Ser Gly Thr Glu Phe Thr Leu Thr Ile Ser Ser Leu Glu Pro
65                  70                  75                  80

Glu Asp Val Gly Leu Tyr Tyr Cys Gln Gln Asn Ser Lys Trp Pro Leu
                85                  90                  95

Thr Phe Gly Gly Gly Thr Lys Val Glu Ile Lys
            100                 105

<210> SEQ ID NO 3
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Met Gln Ser Gly Arg Ala Leu Val Gln Pro Gly Glu
1               5                   10                  15

Ser Leu Arg Leu Ser Cys Val Val Ser Gly Leu Ser Phe Ile Asn His
            20                  25                  30

Gly Val Thr Gln Val Arg Gln Ala Pro Gly Lys Met Leu Asp Trp Val
        35                  40                  45

Ser Ser Thr Asp Thr Ala Gly Gly Pro Phe Cys Val Asp Ser Val
50                  55                  60

Lys Asp Arg Phe Thr Ile Ser Thr Asp Asp Ser Lys Asn Thr Val Ser
65                  70                  75                  80

Leu Glu Ile Asn Ser Met Arg Val Glu Asp Thr Ala Ala Tyr Tyr Cys
                85                  90                  95

Ala Thr Arg Gln Glu Tyr Ser Asp Tyr Tyr Trp Gly Arg Gly Val Pro
            100                 105                 110

Val Thr Val Ser Ser
            115

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Ile Glu Leu Thr Gln Ser Pro Ser Thr Leu Ser Ala Ser Pro Gly
1               5                   10                  15

Glu Arg Val Thr Leu Ser Cys Arg Ala Ser Gln Ser Val Gly Ser Arg
            20                  25                  30

Leu Ala Trp Tyr His Gln Ser Pro Gly Gln Ala Pro Arg Leu Leu Ile
        35                  40                  45

Tyr Gly Ala Ser Ser Arg Pro Thr Gly Ile Pro Asp Arg Phe Ser Ala
50                  55                  60

Ser Gly Ser Gly Thr Glu Phe Thr Leu Thr Ile Ser Ser Leu Glu Pro
65                  70                  75                  80

Glu Asp Val Gly Leu Tyr Tyr Cys Gln Gln Asn Tyr Lys Trp Pro Leu
                85                  90                  95

Thr Phe Gly Gly Gly Thr Lys Val Glu Ile Lys
            100                 105

<210> SEQ ID NO 5
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Asp Tyr
            20                  25                  30

Tyr Met Asp Trp Ile Arg Gln Ala Pro Gly Lys Gly Leu Glu Trp Val
        35                  40                  45

Ser Arg Ile Ser Pro Gly Gly Asp Val Thr Trp Tyr Ala Asp Ser Val
50                  55                  60

```
Lys Gly Arg Phe Thr Ile Ser Arg Asp Asn Ala Gln Ser Leu Tyr Leu
 65                  70                  75                  80

Gln Met Asn Ser Leu Arg Ala Glu Asp Thr Ala Val Tyr Phe Cys Ala
                 85                  90                  95

Arg Asp Asp Ile Val Val Ser Arg Ile Phe Asp Asp Trp Gly Gln Gly
            100                 105                 110

Thr Leu Val Thr Val Ser Ser
        115

<210> SEQ ID NO 6
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Arg Ser Tyr
            20                  25                  30

Leu Ala Trp Tyr Gln Gln Lys Pro Gly Lys Ala Pro Lys Leu Leu Ile
        35                  40                  45

Tyr Asp Ala Ala His Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Arg Asn Ser Tyr Pro Leu
                 85                  90                  95

Thr Phe Gly Gly Gly Thr Lys Val Glu Ile Lys
            100                 105

<210> SEQ ID NO 7
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Glu Gln Ser Gly Ala Glu Val Arg Glu Pro Gly Ala
 1               5                  10                  15

Ser Val Lys Val Ser Cys Lys Ala Ser Gly Leu Thr Ser Gly Ser Tyr
            20                  25                  30

Ala Ile Thr Trp Val Arg Gln Ala Pro Gly Gln Gly Leu Glu Trp Met
        35                  40                  45

Gly Val Ile Ile Pro Leu Val Gly Val Thr Asn Tyr Ala Glu Lys Phe
 50                  55                  60

Gln Gly Arg Val Thr Phe Thr Ala Asp Thr Ser Thr Ser Thr Ala Tyr
 65                  70                  75                  80

Met Glu Leu Thr Ser Leu Arg Ser Asp Asp Thr Ala Thr Tyr Tyr Cys
                 85                  90                  95

Ala Arg Asp Pro Phe Cys Ser Gly Asn Gly Cys Tyr Gly Tyr Tyr Asp
            100                 105                 110

Val Trp Gly Pro Gly Val Lys Val Thr Val Ser Ser
        115                 120
```

```
<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Glu Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Ser Ser Ala Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Ser
65                  70                  75                  80

Glu Asp Phe Ala Thr Tyr Tyr Cys Gln Gln Tyr Asn Ser Val Pro Leu
                85                  90                  95

Thr Phe Gly Gly Gly Thr Lys Val Glu Met Lys
            100                 105

<210> SEQ ID NO 9
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Leu Glu Ser Gly Gly Asp Leu Val Gln Pro Gly Glu
1               5                   10                  15

Ser Leu Arg Leu Ser Cys Val Val Ser Gly Ile Ser Phe Ser Asn His
            20                  25                  30

Gly Met Thr Trp Val Arg Gln Ala Pro Gly Lys Gly Leu Asp Trp Val
        35                  40                  45

Ser Ser Ile Asp Ser Asp Gly Gly Thr Phe Tyr Ala Asp Ser Val
    50                  55                  60

Lys Gly Arg Phe Thr Ile Ser Arg Asp Asp Ser Asn Asn Thr Val Ser
65                  70                  75                  80

Leu Gln Met Asn Ser Leu Arg Val Glu Asp Thr Ala Val Tyr Tyr Cys
                85                  90                  95

Ala Ala Arg His Glu Tyr Ser Asp Tyr Tyr Trp Gly Arg Gly Val Pro
            100                 105                 110

Val Thr Val Ser Ser
        115

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10
```

```
Asp Ile Glu Leu Thr Gln Ser Pro Ser Ile Leu Ser Val Ser Pro Gly
1               5                   10                  15

Glu Arg Ala Thr Leu Ser Cys Arg Ala Ser Gln Ser Val Gly Asn Arg
            20                  25                  30

Leu Ala Trp Tyr His Gln Arg Pro Gly Gln Ala Pro Arg Leu Leu Ile
            35                  40                  45

Tyr Gly Ala Ser Ser Arg Pro Thr Gly Ile Pro Asp Arg Phe Ser Ala
    50                  55                  60

Ser Gly Ser Gly Thr Glu Phe Thr Leu Thr Ile Ser Ser Leu Glu Pro
65                  70                  75                  80

Glu Asp Val Gly Val Tyr Tyr Cys Gln Gln Asn Ser Lys Trp Pro Leu
                85                  90                  95

Thr Phe Gly Gly Gly Thr Lys Val Glu Ile Lys
            100                 105
```

<210> SEQ ID NO 11
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Glu Val Gln Leu Val Glu Ser Gly Arg Ala Cys Ile Gln Pro Gly Glu
1               5                   10                  15

Ser Leu Arg Leu Ser Cys Val Ile Tyr Gly Leu Ser Phe Ser Asn His
            20                  25                  30

Gly Val Thr Gln Val Arg Gln Ala Thr Gly Lys Val Leu Asp Trp Val
            35                  40                  45

Cys Ser Thr Asp Thr Asp Gly Gly Thr Cys Cys Val Asp Ser Val
    50                  55                  60

Lys Asp Arg Phe Thr Ile Ser Arg Asp Ser Lys Asn Thr Val Ser
65                  70                  75                  80

Leu Glu Met Asn Ser Met Arg Val Glu Asp Thr Ala Ala Tyr Tyr Cys
                85                  90                  95

Ala Thr Arg Gln Glu Tyr Ser Asp Tyr Tyr Trp Gly Arg Gly Val Pro
            100                 105                 110

Val Thr Val Ser Ser
        115
```

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Glu Ile Glu Leu Thr Gln Ser Pro Ser Thr Leu Ser Ala Ser Pro Gly
1               5                   10                  15

Glu Arg Val Thr Leu Ser Cys Arg Ala Ser Gln Ser Val Gly Ser Arg
            20                  25                  30

Leu Ala Trp Tyr His Gln Ser Pro Gly Gln Ala Pro Arg Leu Leu Ile
            35                  40                  45

Tyr Gly Ala Ser Ser Arg Pro Thr Gly Ile Pro Asp Arg Phe Ser Ala
    50                  55                  60
```

```
Ser Gly Ser Gly Thr Glu Phe Thr Leu Thr Ile Ser Ser Leu Glu Pro
 65                  70                  75                  80

Glu Asp Val Gly Leu Tyr Tyr Cys Gln Gln Asn Tyr Lys Trp Pro Leu
                 85                  90                  95

Thr Phe Gly Gly Gly Thr Lys Val Glu Ile Lys
            100                 105

<210> SEQ ID NO 13
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Gln Ser Gly Gly Gly Leu Val Gln Pro Gly Glu
 1               5                  10                  15

Ser Leu Arg Leu Ser Cys Val Val Ser Gly Leu Ser Phe Ser Asn His
                 20                  25                  30

Gly Val Thr Trp Val Arg Gln Ala Pro Gly Lys Gly Leu Asp Trp Val
             35                  40                  45

Ser Ser Ile Asp Thr Asp Gly Gly Thr Phe Tyr Gly Asp Ser Val
 50                  55                  60

Lys Gly Arg Phe Thr Ile Ser Arg Asp Asp Ser Lys Asn Thr Val Ser
 65                  70                  75                  80

Leu Glu Met Asn Ser Leu Arg Val Glu Asp Thr Ala Val Tyr Tyr Cys
                 85                  90                  95

Ala Ala Arg Gln Glu Tyr Ser Asp Tyr Tyr Trp Gly Arg Gly Val Pro
            100                 105                 110

Val Thr Val Ser Ser
            115

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Glu Leu Thr Gln Ser Pro Ser Thr Leu Ser Val Ser Pro Gly
 1               5                  10                  15

Glu Arg Ala Thr Leu Ser Cys Arg Ala Ser Gln Ser Val Gly Ser Arg
                 20                  25                  30

Leu Ala Trp Tyr His Gln Arg Pro Gly Gln Ala Pro Arg Leu Leu Ile
             35                  40                  45

Tyr Gly Ala Ser Ser Arg Pro Thr Gly Ile Pro Asp Arg Phe Ser Gly
 50                  55                  60

Ser Gly Ser Gly Thr Glu Phe Thr Leu Thr Ile Ser Ser Leu Glu Pro
 65                  70                  75                  80

Glu Asp Val Gly Leu Tyr Tyr Cys Gln Gln Asn Ser Lys Trp Pro Leu
                 85                  90                  95

Thr Phe Gly Gly Gly Thr Lys Val Glu Ile Lys
            100                 105

<210> SEQ ID NO 15
<211> LENGTH: 124
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Glu Gln Ser Gly Ala Glu Val Lys Lys Pro Gly Ala
1               5                   10                  15

Ser Val Lys Val Ser Cys Lys Ala Ser Gly Phe Thr Ser Gly Ser Tyr
            20                  25                  30

Ala Ile Ser Trp Val Arg Gln Ala Pro Gly Gln Gly Leu Glu Trp Met
        35                  40                  45

Gly Val Ile Ile Pro Leu Val Gly Val Thr Asn Tyr Ala Glu Lys Phe
    50                  55                  60

Gln Gly Arg Val Thr Phe Thr Ala Asp Thr Ser Thr Ser Thr Ala Tyr
65                  70                  75                  80

Met Glu Leu Ser Ser Leu Arg Ser Glu Asp Thr Ala Thr Tyr Phe Cys
                85                  90                  95

Ala Arg Asp Pro Tyr Cys Ser Gly Asn Gly Cys Tyr Gly Trp Tyr Asp
            100                 105                 110

Val Trp Gly Pro Gly Val Leu Val Thr Val Ser Ser
            115                 120

<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Glu Leu Thr Gln Ser Pro Ser Leu Ser Ala Ser Val Gly
1               5                   10                  15

Asp Lys Val Thr Ile Ser Cys Arg Ala Ser Gln Tyr Ile Lys Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Gln Ser Gly Val Pro Ser Arg Phe Ser Gly
    50                  55                  60

Ser Gly Ser Gly Thr Asp Phe Thr Leu Thr Ile Thr Asn Val Gln Pro
65                  70                  75                  80

Glu Asp Phe Ala Thr Tyr Tyr Cys Gln Gln Tyr Asp Ser Ala Pro Phe
                85                  90                  95

Thr Phe Gly Pro Gly Thr Lys Leu Asp Ile Arg
            100                 105

<210> SEQ ID NO 17
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Glu Ser Gly Gly Gly Leu Val Gln Pro Gly Glu
1               5                   10                  15

Ser Leu Arg Leu Ser Cys Val Val Ser Gly Leu Ser Phe Ser Asn His

```
            20                  25                  30
Gly Val Thr Trp Val Arg Gln Ala Pro Gly Lys Gly Leu Asp Trp Val
        35                  40                  45

Ser Ser Ile Asp Thr Asp Gly Gly Thr Phe Tyr Gly Asp Ser Val
    50                  55                  60

Lys Gly Arg Phe Thr Ile Ser Arg Asp Asn Ser Lys Ser Thr Val Ser
65                  70                  75                  80

Leu Glu Met Asn Ser Leu Arg Val Glu Asp Thr Ala Val Tyr Tyr Cys
                85                  90                  95

Ala Ala Arg Gln Glu Tyr Ser Asp Tyr Tyr Trp Gly Arg Gly Val Leu
            100                 105                 110

Val Thr Val Ser Ser
        115

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Glu Leu Thr Gln Ser Pro Ala Ile Leu Ser Leu Ser Pro Gly
1               5                   10                  15

Glu Arg Ala Thr Leu Leu Cys Arg Ala Ser Gln Asn Val Gly Asn Arg
            20                  25                  30

Leu Ala Trp Tyr His Gln Arg Pro Gly Gln Ala Pro Arg Leu Leu Ile
        35                  40                  45

Tyr Gly Ala Ser Ser Arg Pro Thr Gly Ile Pro Asp Arg Phe Ser Gly
    50                  55                  60

Ser Gly Ser Gly Thr Glu Phe Thr Leu Thr Ile Ser Ser Leu Glu Pro
65                  70                  75                  80

Glu Asp Val Gly Val Tyr Tyr Cys Gln Gln Asp Ser Asn Trp Pro Leu
                85                  90                  95

Thr Phe Gly Gly Gly Thr Arg Val Glu Ile Lys
            100                 105

<210> SEQ ID NO 19
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Glu Ser Gly Gly Leu Val Gln Pro Gly Glu
1               5                   10                  15

Ser Leu Arg Leu Ser Cys Val Ser Gly Leu Ser Phe Ser Asn His
            20                  25                  30

Gly Val Thr Trp Val Arg Gln Ala Pro Gly Lys Gly Leu Asp Trp Val
        35                  40                  45

Ser Ser Ile Asp Thr Asp Gly Gly Thr Phe Tyr Gly Asp Ser Val
    50                  55                  60

Lys Gly Arg Phe Thr Ile Ser Arg Asp Asn Ser Lys Ser Thr Val Ser
65                  70                  75                  80

Leu Glu Met Asn Ser Leu Arg Val Glu Asp Thr Ala Val Tyr Tyr Cys
```

Ala Ala Arg Gln Glu Tyr Ser Asp Tyr Tyr Trp Gly Arg Gly Val Leu
            100                 105                 110

Val Thr Val Ser Ser
        115

<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Ile Glu Leu Thr Gln Ser Pro Ser Thr Leu Ser Val Ser Pro Gly
1               5                   10                  15

Glu Arg Ala Thr Leu Ser Cys Arg Ala Ser Gln Ser Val Gly Ser Arg
            20                  25                  30

Leu Ala Trp Tyr His Gln Ser Pro Gly Gln Ala Pro Arg Leu Leu Ile
        35                  40                  45

Tyr Gly Ala Ser Ser Arg Pro Thr Gly Ile Pro Asp Arg Phe Ser Ala
    50                  55                  60

Ser Gly Ser Gly Thr Glu Phe Thr Leu Thr Ile Ser Ser Leu Glu Pro
65                  70                  75                  80

Glu Asp Val Gly Leu Tyr Tyr Cys Gln Gln Asn Ser Lys Trp Pro Leu
                85                  90                  95

Thr Phe Gly Gly Gly Thr Lys Val Glu Ile Lys
            100                 105

<210> SEQ ID NO 21
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Val Gln Ser Gly Gly Ala Leu Val Gln Pro Gly Glu
1               5                   10                  15

Ser Leu Arg Leu Ser Cys Val Val Ser Gly Leu Ser Phe Ser Asn His
            20                  25                  30

Gly Val Thr Arg Val Arg Gln Ala Pro Gly Lys Gly Leu Asp Trp Val
        35                  40                  45

Ser Ser Thr Asp Thr Asp Gly Gly Thr Phe Tyr Gly Asp Ser Val
    50                  55                  60

Lys Gly Arg Phe Thr Ile Ser Arg Asp Asp Ser Lys Asn Thr Val Ser
65                  70                  75                  80

Leu Glu Met Asn Ser Leu Arg Val Glu Asp Thr Ala Ala Tyr Tyr Cys
                85                  90                  95

Ala Ala Arg Gln Glu Tyr Ser Asp Tyr Tyr Trp Gly Arg Gly Val Pro
            100                 105                 110

Val Thr Val Ser Ser
        115

<210> SEQ ID NO 22
<211> LENGTH: 107
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 22

```
Glu Ile Glu Leu Thr Gln Ser Pro Ser Thr Leu Ser Val Ser Pro Gly
1               5                   10                  15
Glu Arg Ala Thr Leu Ser Cys Arg Ala Ser Gln Ser Val Gly Ser Arg
            20                  25                  30
Leu Ala Trp Tyr His Gln Ser Pro Gly Gln Ala Pro Arg Leu Leu Ile
        35                  40                  45
Tyr Gly Ala Ser Ser Arg Pro Thr Gly Ile Pro Asp Arg Phe Ser Ala
    50                  55                  60
Ser Gly Ser Gly Thr Glu Phe Thr Leu Thr Ile Ser Ser Leu Glu Pro
65                  70                  75                  80
Glu Asp Val Gly Leu Tyr Tyr Cys Gln Gln Asn Tyr Lys Trp Pro Leu
                85                  90                  95
Thr Phe Gly Gly Gly Thr Lys Val Glu Ile Lys
            100                 105
```

<210> SEQ ID NO 23
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Gln Val Gln Leu Leu Glu Ser Gly Pro Gly Leu Val Lys Pro Ser Glu
1               5                   10                  15
Thr Leu Ser Leu Asn Cys Thr Val Thr Gly Asp Thr Leu Tyr Gly Gly
            20                  25                  30
Phe Gly Trp Gly Trp Ile Arg Gln Pro Pro Gly Lys Gly Leu Glu Trp
        35                  40                  45
Ile Gly Asn Ile Tyr Ser His Asp Gly Ser Thr Phe Tyr Asn Pro Ser
    50                  55                  60
Leu Lys Gly Arg Val Ser Ile Ser Thr Asp Thr Ser Lys Asn Gln Phe
65                  70                  75                  80
Ser Leu Arg Met Asp Ser Val Ser Ala Ala Asp Ala Ala Val Tyr Phe
                85                  90                  95
Cys Val Arg Ser Arg Ser Thr His Tyr Tyr Ser Gly Tyr Ser His
            100                 105                 110
Ser Phe Tyr Tyr Trp Gly Gln Gly Val Leu Val Ser Val Ser Ser
        115                 120                 125
```

<210> SEQ ID NO 24
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Glu Ile Glu Leu Thr Gln Ser Pro Ser Leu Ser Val Ser Val Gly
1               5                   10                  15
Asp Lys Val Thr Ile Thr Cys Arg Ala Ser Gln Asp Ile Ser Ser Tyr
            20                  25                  30
```

```
Leu Thr Trp Tyr Gln Gln Lys Pro Gly Lys Ala Cys Lys Leu Leu Ile
            35                  40                  45

Ser Ala Ala Ser Ser Leu Gln Ser Gly Val Pro Ser Arg Phe Ser Gly
 50                  55                  60

Ser Gly Ser Gly Thr Asp Phe Thr Leu Thr Ile Asp Ser Leu Gln Pro
 65                  70                  75                  80

Glu Asp Phe Gly Thr Tyr Tyr Cys Gln Gln Tyr Tyr Ser Ala Pro Leu
                85                  90                  95

Phe Phe Gly Gly Gly Thr Lys Val Glu Ile Lys
               100                 105
```

```
<210> SEQ ID NO 25
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Leu Glu Ser Gly Gly Gly Leu Val Gln Pro Gly Glu
 1                5                  10                  15

Ser Leu Arg Leu Ser Cys Val Val Ser Gly Leu Ser Phe Ser Asn His
                20                  25                  30

Gly Val Thr Trp Val Arg Gln Ala Pro Gly Lys Gly Leu Asp Trp Val
            35                  40                  45

Ser Ser Ile Asp Thr Asp Gly Gly Thr Phe Tyr Gly Asp Ser Val
 50                  55                  60

Lys Gly Arg Phe Thr Ile Ser Arg Asp Asp Ser Lys Asn Thr Val Ser
 65                  70                  75                  80

Leu Glu Met Asn Ser Leu Arg Val Glu Asp Thr Ala Val Tyr Tyr Cys
                85                  90                  95

Ala Ala Arg Gln Glu Tyr Ser Asp Tyr Tyr Trp Gly Arg Gly Val Pro
               100                 105                 110

Val Thr Val Ser Ser
         115
```

```
<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Ile Glu Leu Thr Gln Ser Pro Ser Thr Leu Ser Val Ser Pro Gly
 1                5                  10                  15

Glu Arg Ala Thr Leu Ser Cys Arg Ala Ser Gln Ser Val Gly Ser Arg
                20                  25                  30

Leu Ala Trp Tyr His Gln Ser Pro Gly Gln Ala Pro Arg Leu Leu Ile
            35                  40                  45

Tyr Gly Ala Ser Ser Arg Pro Thr Gly Ile Pro Asp Arg Phe Ser Ala
 50                  55                  60

Ser Gly Ser Gly Thr Glu Phe Thr Leu Thr Ile Ser Ser Leu Glu Pro
 65                  70                  75                  80

Glu Asp Val Gly Leu Tyr Tyr Cys Gln Gln Asn Ser Lys Trp Pro Leu
                85                  90                  95
```

Thr Phe Gly Gly Gly Thr Lys Val Glu Ile Lys
            100                 105

<210> SEQ ID NO 27
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Leu Glu Ser Gly Gly Leu Val Gln Pro Gly Glu
1               5                   10                  15

Ser Leu Arg Leu Ser Cys Val Val Ser Gly Leu Ser Phe Ser Asn His
                20                  25                  30

Gly Val Thr Trp Val Arg Gln Ala Pro Gly Lys Gly Leu Asp Trp Val
            35                  40                  45

Ser Ser Ile Asp Thr Asp Gly Gly Thr Phe Tyr Gly Asp Ser Val
50                  55                  60

Lys Gly Arg Phe Thr Ile Ser Arg Asp Asp Ser Lys Asn Thr Val Ser
65                  70                  75                  80

Leu Glu Met Asn Ser Leu Arg Val Glu Asp Thr Ala Val Tyr Tyr Cys
                85                  90                  95

Ala Ala Arg Gln Glu Tyr Ser Asp Tyr Tyr Trp Gly Arg Gly Val Pro
            100                 105                 110

Val Thr Val Ser Ser
        115

<210> SEQ ID NO 28
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Glu Leu Thr Gln Ser Pro Ala Ile Leu Ser Leu Ser Pro Gly
1               5                   10                  15

Glu Arg Ala Thr Leu Leu Cys Arg Ala Ser Gln Asn Val Gly Asn Arg
                20                  25                  30

Leu Ala Trp Tyr His Gln Arg Pro Gly Gln Ala Pro Arg Leu Leu Ile
            35                  40                  45

Tyr Gly Ala Ser Ser Arg Pro Thr Gly Ile Pro Asp Arg Phe Ser Gly
        50                  55                  60

Ser Gly Ser Gly Thr Glu Phe Thr Leu Thr Ile Ser Ser Leu Glu Pro
65                  70                  75                  80

Glu Asp Val Gly Val Tyr Tyr Cys Gln Gln Asp Ser Asn Trp Pro Leu
                85                  90                  95

Thr Phe Gly Gly Gly Thr Arg Val Glu Ile Lys
            100                 105

<210> SEQ ID NO 29
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Leu Glu Ser Gly Gly Asp Leu Val Gln Pro Gly Glu
1               5                   10                  15

Ser Leu Arg Leu Ser Cys Val Ala Ser Gly Ile Ser Phe Ser Asn His
            20                  25                  30

Gly Met Thr Trp Val Arg Gln Ala Pro Gly Lys Gly Leu Asp Trp Val
        35                  40                  45

Ser Ser Ile Asp Ser Asp Gly Gly Thr Phe Tyr Ala Asp Ser Val
    50                  55                  60

Lys Gly Arg Phe Thr Ile Ser Arg Asp Asn Ser Asn Asn Thr Val Ser
65                  70                  75                  80

Leu Gln Met Asn Ser Leu Arg Ala Glu Asp Thr Ala Val Tyr Phe Cys
                85                  90                  95

Ala Ala Arg His Glu Tyr Ser Asp Tyr Tyr Trp Gly Gln Gly Val Leu
                100                 105                 110

Val Thr Val Ser Ser
        115

<210> SEQ ID NO 30
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Glu Leu Thr Gln Ser Pro Ala Ile Leu Ser Leu Ser Pro Gly
1               5                   10                  15

Glu Arg Ala Thr Leu Leu Cys Arg Ala Ser Gln Asn Val Gly Asn Arg
            20                  25                  30

Leu Ala Trp Tyr His Gln Arg Pro Gly Gln Ala Pro Arg Leu Leu Ile
        35                  40                  45

Tyr Gly Ala Ser Ser Arg Pro Thr Gly Ile Pro Asp Arg Phe Ser Gly
    50                  55                  60

Ser Gly Ser Gly Thr Glu Phe Thr Leu Thr Ile Ser Ser Leu Glu Pro
65                  70                  75                  80

Glu Asp Val Gly Val Tyr Tyr Cys Gln Gln Asp Ser Asn Trp Pro Leu
                85                  90                  95

Thr Phe Gly Gly Gly Thr Arg Val Glu Ile Lys
                100                 105

<210> SEQ ID NO 31
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Leu Glu Ser Gly Gly Gly Leu Val Gln Pro Gly Glu
1               5                   10                  15

Ser Leu Arg Leu Ser Cys Val Val Ser Gly Leu Ser Phe Ser Asn His
            20                  25                  30

Gly Val Thr Trp Val Arg Gln Ala Pro Gly Lys Gly Leu Asp Trp Val
        35                  40                  45

```
Ser Ser Ile Asp Thr Asp Gly Gly Thr Phe Tyr Gly Asp Ser Val
    50                  55                  60

Lys Gly Arg Phe Thr Ile Ser Arg Asp Asp Ser Lys Asn Thr Val Ser
 65                  70                  75                  80

Leu Glu Met Asn Ser Leu Arg Val Glu Asp Thr Ala Val Tyr Tyr Cys
                 85                  90                  95

Ala Ala Arg Gln Glu Tyr Ser Asp Tyr Tyr Trp Gly Arg Gly Val Pro
            100                 105                 110

Val Thr Val Ser Ser
            115

<210> SEQ ID NO 32
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Leu Gln Met Thr Gln Ser Pro Ala Thr Leu Ser Leu Ser Pro Gly
 1               5                  10                  15

Glu Arg Ala Thr Leu Ser Cys Arg Ala Ser Gln Ser Val Gly Asp Arg
                20                  25                  30

Leu Ala Trp Tyr His Gln Ser Pro Gly Gln Ala Pro Arg Leu Leu Ile
            35                  40                  45

Tyr Gly Ala Ser Asn Arg Pro Thr Gly Ile Ser Asp Arg Phe Arg Gly
     50                  55                  60

Ser Gly Ser Gly Thr Glu Phe Ile Leu Thr Ile Ser Ser Leu Glu Pro
 65                  70                  75                  80

Glu Asp Val Gly Val Tyr Tyr Cys Gln Gln Asp Ser Ser Trp Pro Leu
                 85                  90                  95

Thr Phe Gly Gly Gly Thr Lys Val Glu Ile Lys
            100                 105

<210> SEQ ID NO 33
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Leu Glu Ser Gly Gly Gly Leu Val Gln Pro Gly Glu
 1               5                  10                  15

Ser Leu Arg Leu Pro Cys Ala Ala Ser Gly Phe Thr Phe Ser Gly Tyr
                20                  25                  30

Gly Met Ser Trp Val Arg Gln Ala Pro Gly Lys Gly Leu Glu Trp Val
            35                  40                  45

Ser Ser Ile Asp Ser Ser Gly Gly Glu Thr Tyr Tyr Ala Asp Ser Val
     50                  55                  60

Lys Gly Arg Phe Thr Ile Ser Arg Asp Asn Ser Lys Asn Met Leu Tyr
 65                  70                  75                  80

Leu Gln Met Asn Asn Leu Arg Ala Glu Asp Thr Ala Val Tyr Tyr Cys
                 85                  90                  95

Ala Ala Arg His Glu Tyr Ser Asp Tyr Tyr Trp Gly Gln Gly Val Leu
            100                 105                 110
```

Val Thr Val Ser Ser
        115

<210> SEQ ID NO 34
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Glu Leu Thr Gln Ser Pro Ser Thr Leu Ser Val Ser Pro Gly
1               5                   10                  15

Glu Arg Ala Thr Leu Ser Cys Arg Ala Ser Gln Ser Val Gly Ser Arg
            20                  25                  30

Leu Ala Trp Tyr His Gln Ser Pro Gly Gln Ala Pro Arg Leu Leu Ile
        35                  40                  45

Tyr Gly Ala Ser Ser Arg Pro Thr Gly Ile Pro Asp Arg Phe Ser Ala
    50                  55                  60

Ser Gly Ser Gly Thr Glu Phe Thr Leu Thr Ile Ser Ser Leu Glu Pro
65                  70                  75                  80

Glu Asp Val Gly Leu Tyr Tyr Cys Gln Gln Asn Ser Lys Trp Pro Leu
                85                  90                  95

Thr Phe Gly Gly Gly Thr Lys Val Glu Ile Lys
            100                 105

<210> SEQ ID NO 35
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Gln Leu Val Gln Ser Gly Gly Gly Leu Val Gln Pro Gly Glu
1               5                   10                  15

Ser Leu Arg Leu Ser Cys Val Val Ser Gly Leu Ser Phe Ser Asn His
            20                  25                  30

Gly Val Thr Trp Val Arg Gln Ala Pro Gly Lys Gly Leu Asp Trp Val
        35                  40                  45

Ser Ser Ile Asp Thr Asp Gly Gly Thr Phe Tyr Gly Asp Ser Val
    50                  55                  60

Lys Gly Arg Phe Thr Ile Ser Arg Asp Asp Ser Lys Asn Thr Val Ser
65                  70                  75                  80

Leu Glu Met Asn Ser Leu Arg Val Glu Asp Thr Ala Val Tyr Tyr Cys
                85                  90                  95

Ala Ala Arg Gln Glu Tyr Ser Asp Tyr Tyr Trp Gly Arg Gly Val Pro
            100                 105                 110

Val Thr Val Ser Ser
        115

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 36

Glu Ile Glu Leu Thr Gln Ser Pro Ser Thr Leu Ser Val Ser Pro Gly
1               5                   10                  15

Glu Arg Ala Thr Leu Ser Cys Arg Ala Ser Gln Ser Val Gly Ser Arg
            20                  25                  30

Leu Ala Trp Tyr His Gln Ser Pro Gly Gln Ala Pro Arg Leu Leu Ile
        35                  40                  45

Tyr Gly Ala Ser Ser Arg Pro Thr Gly Ile Pro Asp Arg Phe Ser Ala
    50                  55                  60

Ser Gly Ser Gly Thr Glu Phe Thr Leu Thr Ile Ser Ser Leu Glu Pro
65                  70                  75                  80

Glu Asp Val Gly Leu Tyr Tyr Cys Gln Gln Asn Ser Lys Trp Pro Leu
                85                  90                  95

Thr Phe Gly Gly Gly Thr Lys Val Glu Ile Lys
            100                 105
```

What is claimed is:

1. A composition comprising a reactive anti-Marburg immunoglobulin and a pharmaceutically acceptable carrier, wherein the immunoglobulin comprises VH complementarity determining regions (CDRs) of:
   a VH CDR1 corresponding to amino acid residues of 26-33 of SEQ ID NO: 1;
   a VH CDR2 corresponding to amino acid residues of 51-58 of SEQ ID NO: 1; and
   a VH CDR3 corresponding to amino acid residues of 97-107 of SEQ ID NO: 1;
and VL CDRs of:
   a VL CDR1 corresponding to amino acid residues of 27-32 of SEQ ID NO: 2;
   a VL CDR2 corresponding to amino acid residues of 50-52 of SEQ ID NO: 2; and
   a VL CDR3 corresponding to amino acid residues of 89-97 of SEQ ID NO: 2.

2. The composition of claim 1, wherein said composition is reactive to a strain of Marburg virus.

3. The composition of claim 2, wherein the Marburg virus strain is Ci67, Ravn, Musoke, or Angola.

4. The composition of claim 1, wherein the composition further comprises at least one other immunoglobulin selected from the group consisting of:
   (a) immunoglobulin R4G7 having a variable heavy chain (VH) of SEQ ID NO: 9 and a variable light chain (VL) of SEQ ID NO: 10;
   (b) immunoglobulin R4G10 having a VH of SEQ ID NO: 11 and a VL of SEQ ID NO: 12;
   (c) immunoglobulin R4G11 having a VH of SEQ ID NO: 13 and a VL of SEQ ID NO: 14;
   (d) immunoglobulin R3C4 having a VH of SEQ ID NO: 15 and a VL of SEQ ID NO: 16;
   (e) immunoglobulin R4G8 having a VH of SEQ ID NO: 17 and a VL of SEQ ID NO: 18;
   (f) immunoglobulin R3D4 having a VH of SEQ ID NO: 19 and a VL of SEQ ID NO: 20;
   (g) immunoglobulin R3G2 having a VH of SEQ ID NO: 21 and a VL of SEQ ID NO: 22;
   (h) immunoglobulin R3G5 having a VH of SEQ ID NO: 23 and a VL of SEQ ID NO: 24;
   (i) immunoglobulin R4H12 having a VH of SEQ ID NO: 25 and a VL of SEQ ID NO: 26; and
   (j) immunoglobulin R3H2 having a VH of SEQ ID NO: 27 and a VL of SEQ ID NO: 28.

5. The composition of claim 1, wherein the immunoglobulin has at least 90% sequence identity respectively to VH and VL sequences of SEQ ID NO: 1 and 2.

6. The composition of claim 1, wherein the strain of Marburg virus is selected from the group consisting of Ci67, Ravn, Musoke, and Angola.

7. The composition of claim 1, wherein the anti-Marburg virus immunoglobulin is R3F6 having a variable heavy chain of SEQ ID NO: 1 and a variable light chain of SEQ ID NO: 2.

8. The composition of claim 1, wherein the immunoglobulin is a bispecific antibody, a scFv, a Fab, or a diabody.

9. The composition of claim 1, wherein the immunoglobulin is a humanized antibody.

10. A method of protecting a subject from exposure to a Marburg virus strain comprising administering to said subject an effective amount of the composition of claim 1 prior to exposure to said Marburg virus.

11. The method of claim 10, wherein the composition comprises an immunoglobulin that is engineered for extended release, and wherein said the effective amount is an amount of about 5 to about 50 mg/kg of subject weight.

12. The method of claim 10, wherein the subject is administered the composition more than once.

13. A method of inhibiting progression of a Marburg virus infection in a subject after the subject is exposed to said Marburg virus comprising administering at least one effective amount of the composition of claim 1.

14. The method of claim 13, wherein the effective amount of the composition is administered within one week after exposure to a Marburg virus, wherein the composition is administered intravenously or subcutaneously at a dosage of about 25 to about 150 mg/kg of subject weight.

15. The composition of claim 1, wherein the immunoglobulin has at least 95% sequence identity respectively to VH and VL sequences of SEQ ID NO: 1 and 2.

16. The composition of claim 1, wherein the immunoglobulin has at least 97% sequence identity respectively to VH and VL sequences of SEQ ID NO: 1 and 2.

17. The composition of claim 1, wherein the immunoglobulin has at least 98% sequence identity respectively to VH and VL sequences of SEQ ID NO: 1 and 2.

18. The composition of claim 1, wherein the immunoglobulin has at least 99% sequence identity respectively to VH and VL sequences of SEQ ID NO: 1 and 2.

19. An immunoglobulin that is reactive to a strain of Marburg virus, wherein the immunoglobulin is selected from the group consisting of:
- (a) an immunoglobulin comprising VH complementarity determining regions (CDRs) of:
  a VH CDR1 corresponding to amino acid residues of 26-33 of SEQ ID NO: 1;
  a VH CDR2 corresponding to amino acid residues of 51-58 of SEQ ID NO: 1; and
  a VH CDR3 corresponding to amino acid residues of 97-107 of SEQ ID NO: 1;
  and VL CDRs of:
  a VL CDR1 corresponding to amino acid residues of 27-32 of SEQ ID NO: 2;
  a VL CDR2 corresponding to amino acid residues of 50-52 of SEQ ID NO: 2; and
  a VL CDR3 corresponding to amino acid residues of 89-97 of SEQ ID NO: 2;
- (b) immunoglobulin R4G7 having a VH of SEQ ID NO: 9 and a VL of SEQ ID NO: 10;
- (c) immunoglobulin R4G10 having a VH of SEQ ID NO: 11 and a VL of SEQ ID NO: 12;
- (d) immunoglobulin R4G11 having a VH of SEQ ID NO: 13 and a VL of SEQ ID NO: 14;
- (e) immunoglobulin R3C4 having a VH of SEQ ID NO: 15 and a VL of SEQ ID NO: 16;
- (f) immunoglobulin R4G8 having a VH of SEQ ID NO: 17 and a VL of SEQ ID NO: 18;
- (g) immunoglobulin R3D4 having a VH of SEQ ID NO: 19 and a VL of SEQ ID NO: 20;
- (h) immunoglobulin R3G2 having a VH of SEQ ID NO: 21 and a VL of SEQ ID NO: 22;
- (i) immunoglobulin R3G5 having a VH of SEQ ID NO: 23 and a VL of SEQ ID NO: 24;
- (j) immunoglobulin R4H12 having a VH of SEQ ID NO: 25 and a VL of SEQ ID NO: 26; and
- (k) immunoglobulin R3H2 having a VH of SEQ ID NO: 27 and a VL of SEQ ID NO: 28.

* * * * *